United States Patent [19]

Wang et al.

[11] 4,127,501
[45] Nov. 28, 1978

[54] POLYCHROMOPHORIC ULTRAVIOLET STABILIZERS AND THEIR USE IN ORGANIC COMPOSITIONS

[75] Inventors: Richard H. S. Wang; Joseph S. Zannucci, both of Kingsport, Tenn.

[73] Assignee: Eastman Kodak Company, Rochester, N.Y.

[21] Appl. No.: 713,000

[22] Filed: Aug. 9, 1976

Related U.S. Application Data

[62] Division of Ser. No. 502,329, Sep. 3, 1974, abandoned.

[51] Int. Cl.$^2$ .................. C09K 15/20; C08K 5/35; C07D 277/82; C07D 249/18
[52] U.S. Cl. .................. 252/403; 260/45.8 N; 260/45.8 A; 260/45.8 NZ; 260/45.8 SN; 260/45.8 NT; 260/45.8 RW; 260/307 D; 260/308 B; 106/169; 106/304 R; 106/326.15
[58] Field of Search ............ 260/45.8 N, 45.8 A, 260/45.8 NZ, 45.8 SN, 45.8 NT, 45.8 RW; 252/402, 403; 106/169

[56] References Cited

U.S. PATENT DOCUMENTS

| | | | |
|---|---|---|---|
| 3,864,354 | 2/1975 | Irick et al. | 260/45.8 NZ |
| 3,936,419 | 2/1976 | Wang et al. | 260/45.8 NE |
| 3,939,115 | 2/1976 | Wang et al. | 260/45.8 NZ |
| 3,957,813 | 5/1976 | Irick et al. | 260/45.8 R |
| 3,981,822 | 9/1976 | Ownby | 260/45.8 NZ |
| 3,988,295 | 10/1976 | Irick et al. | 260/45.8 NZ |
| 4,000,148 | 12/1976 | Pond et al. | 260/45.8 NZ |
| 4,020,080 | 4/1977 | Irick et al. | 260/45.8 NZ |

*Primary Examiner*—H.S. Cockeram
*Attorney, Agent, or Firm*—Clyde L. Tootle; Daniel B. Reece, III

[57] ABSTRACT

The invention relates to polychromophoric compounds which have been found to be effective ultraviolet stabilizers. The invention also relates to ultraviolet degradable organic compositions containing a stabilizing amount of the polychromophoric composition to prevent such degradation. These stabilizers are effective in the presence of other additives commonly employed in polymeric compositions including, for example, pigments, colorants, fillers, reinforcing agents and the like. These ultraviolet stabilizers may also be incorporated into the organic compositions in the polymer melt or dissolved in the polymer dope, coated on the exterior of the molded article, film or extruded fiber.

86 Claims, No Drawings

POLYCHROMOPHORIC ULTRAVIOLET STABILIZERS AND THEIR USE IN ORGANIC COMPOSITIONS

This is a division of Application Ser. No. 502,329, filed Sept. 3, 1974, now abandoned, which was refiled as Continuation application Ser. No. 829,752, filed Sept. 1, 1977.

This invention relates to polychromophoric ultraviolet stabilizers and their use in organic compositions. More particularly, the invention relates to polychromophoric compositions and the stabilization of ultraviolet degradable organic compositions against deterioration resulting from the exposure to such radiations with such polychromophoric compositions.

The degradative effects of ultraviolet light on various organic compositions is well known in the art. The photo-deterioration or degradation is of particular concern with organic photo-degradable compositions which are exposed to ultraviolet light, such as sunlight, for long periods of time. One group of such photo-degradable organic compositions are polymeric compositions such as polyolefins, polyesters and the like. On exposure to sunlight for extended periods of time, these polymeric compositions degrade and their physical properties are reduced to render the polymeric composition less useful for most applications. Therefore, considerable effort has been directed to providing a solution to the photo-degradation problem of polymeric compositions. As a result of this effort, there have been discovered many additives and stabilizers which improve the stability of polymeric compositions.

Moreover, various additives and stabilizers exhibit the power to absorb ultraviolet radiation within the band of 2900 to 4000 Å. and, when incorporated in various plastic materials such as transparent sheets, the resultant sheet acts as a filter for all the radiation passing through and will transmit only such radiations as are not absorbed by the sheet and/or the absorbing agent. It is thus possible to screen out undesirable radiations and utilize the resulting transparent sheet as a filter in many technical and commercial applications, such as wrappings for food products and the like.

While there are many additives, stabilizers and mixtures thereof which are known in the art to improve the ultraviolet light stability of organic compositions, there is a need in the art for more efficient and effective stabilizers to prevent the photo-degradation of organic compositions susceptible to photo-degradation. Therefore, to provide a more effective and efficient ultraviolet stabilizer for organic compositions susceptible to such degradation would be an advance in the state of the art.

It is, therefore, an object of the present invention to provide more effective and efficient ultraviolet light stabilizer compositions.

Another object of the present invention is to provide useful compositions characterized by improved resistance to ultraviolet degradation and deterioration.

It is still another object of the present invention to provide compositions containing polychromophoric compositions which are resistant to ultraviolet degradation.

It is a still further object of this invention to provide processes for improving the resistance of organic materials to deterioration and degradation by actinic radiation and especially ultraviolet radiation.

It is a still further object of this invention to provide compositions and processes for improving the resistance of organic materials to deterioration and degradation by actinic radiations, including short wave-length visible radiations.

Further objects and advantages of the invention will be apparent to those skilled in the art from the accompanying disclosure and claims.

In accordance with the present invention, polychromophoric compositions are provided which are useful as ultraviolet stabilizers or ultraviolet screening agents. These organic compositions contain at least one heterocyclic group containing compositions connected to a hydroxybenzophenone. The polychromophoric compositions of the present invention have the following structure:

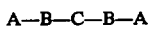

wherein A is a group having the structure

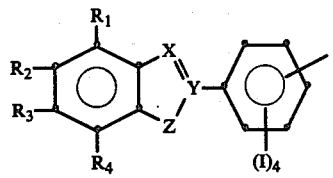

wherein
X and Y are a carbon atom or a nitrogen atom;
Z is an oxygen atom, a sulfur atom, a nitrogen atom, or a nitrogen atom containing a hydrogen atom or an unsubstituted or substituted lower alkyl group having 1 to 12 carbon atoms or an aryl group or substituted aryl group having 6 to 18 carbon atoms;
$R_1$, $R_2$, $R_3$ and $R_4$ are hydrogen, hydroxy, lower alkyl or substituted lower alkyl group having 1 to 12 carbon atoms, cycloalkyl or substituted cycloalkyl, aryl or substituted aryl having 6 to 18 carbon atoms, lower alkylaryl, chloro, bromo, alkoxy, substituted amino, cyano, carboxy and the substituents $R_1$ and $R_2$, $R_2$ and $R_3$, and $R_3$ and $R_4$, combined with the carbon atoms to which they are attached, are joined alkylene groups completing a carbocyclic ring, which ring can also be substituted with one or more of the substituents listed above for $R_1$, $R_2$, $R_3$ and $R_4$;
I is a substituent listed above for $R_1$, $R_2$, $R_3$ and $R_4$ and is present on all positions of the benzenoid ring, except the carbon atom attached to the Y substituent and the carbon atom attached to the B group. The B connecting group is attached to the benzenoid ring in the ortho, meta or para positions from the carbon atom connected to the Y substituent. The I substituents can all be one of the substituents listed above or different listed substituents.

The B group is a group connecting A and C and can be alkylene, arylene, carbonyloxy, oxycarbonylalkyleneoxy, alkyleneoxy, oxycarbonyl, alkylenecarbonyloxy, oxycarbonyloxy, oxyalkylene, alkyleneoxyalkyleneoxy, thio, thioalkyleneoxy, sulfinyldioxy, oxy(alkoxy)phosphinooxy, alkyloxyphosphinylidene, aryloxyphosphinylidene, oxy(alkyl)phosphinyloxy, aminocarbonyl, N-alkylaminocarbonyl, N-arylaminocarbonyl, aminocarbonylalkyleneoxy, N-alkylaminocarbonylalkyleneoxy N-arylaminocarbonylalkyleneoxy, aminocarbonylamino, N-alkylaminocarbonylamino, di(N-alkylamino)carbonyl, N-arylaminocarbonyl, N-alkylaminocarbonyl, di(N-aryl)aminocarbonyl, amino, N-alkylamino, N-arylamino, N-alkylaminoalkyleneoxy, N-arylaminoalkyleneoxy, oxyalkyleneoxy, oxyaryleneoxy, alkyleneaminoalkylene, aryleneaminoarylene, aryleneaminoalkylene and alkyleneaminoarylene.

The C group is a hydroxybenzophenone group having the formula

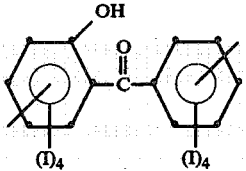

wherein
I is the same substituent as listed above and is present in all positions of the benzenoid ring except the carbon atoms attached to the B groups connecting the A and C moieties. The B connecting groups are attached to the benzenoid ring in the ortho, meta or para positions from the carbonyl group of the benzophenone. The I substituents can be one of the substituents listed above or different listed substituents.

Suitable heterocyclic A groups having the structure

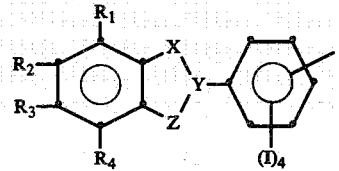

are, for example substituted and unsubstituted benzoxazoles, benzotriazoles, benzothiazoles, indoles and benzimidazoles.

Examples of suitable benzoxazoles are those benzoxazoles having the formula

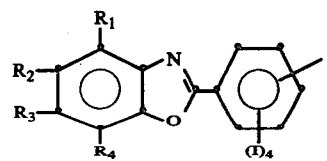

such as 4-(5,6-dimethyl-2-benzoxazolyl)phenyl, 4-(2-benzoxazolyl)-2-chlorophenyl, 3-(5-chloro-2-benzoxazolyl)phenyl.

Examples of suitable benzothiazoles are those having the formula

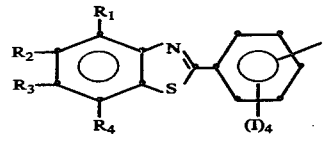

such as 4-(5,6-dimethyl-2-benzothiazolyl)phenyl, 4-(2-benzothiazolyl)-2-chlorophenyl, 3-(5-chloro-2-benzothiazolyl)phenyl.

Examples of suitable benzotriazole moieties are those having the formula

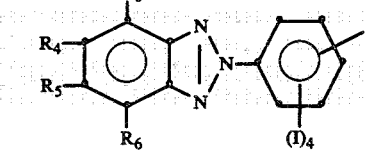

such as 4-(5-chloro-2H-benzotriazol-2-yl)phenyl, 4-(2H-benzotriazol-2-yl)phenyl, and 4-(5-methoxy-2H-benzotriazol-2-yl)phenyl.

Examples of suitable benzimidazoles are those having the formula

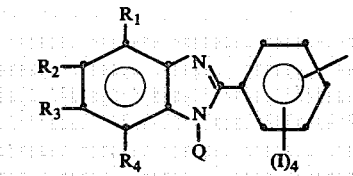

wherein Q is hydrogen or lower alkyl group or substituted alkyl group containing 1 to 12 carbon atoms or aryl substituted aryl containing 6 to 18 carbon atoms such as 4-(5,6-dimethyl-2-benzimidazolyl)phenyl, 4-(2-benzimidazolyl)-2-chlorophenyl, 3-(5-chloro-2-benzimidazolyl)-phenyl, 4-(1-methyl-2-benzimidazolyl)-phenyl, 4-(1-ethyl-5-chloro-2-benzimidazolyl)phenyl.

Examples of suitable indole moieties are those having the formula

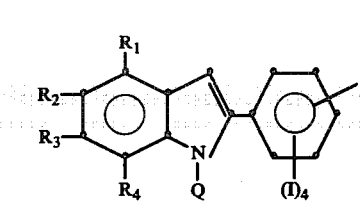

wherein Q is hydrogen or lower alkyl group or substituted alkyl group containing 1 to 12 carbon atoms or aryl or substituted aryl containing 6 to 18 carbon atoms. Such suitable indole moieties are, for example, 3-(1-ethyl-5-cyano-2-indolyl)phenyl, 3-(5-chloro-2-indolyl)-phenyl, 3-(1-methyl-2-indolyl)phenyl, 3-(6-methyl-2-indolyl)phenyl, 3-(6-chloro-2-indolyl)phenyl, 3-(5-acetamido-2-indolyl)phenyl, 3-(2-indolyl)phenyl, 4-(1-ethyl-2-indolyl)phenyl, 4-(5-cyano-2-indolyl)phenyl, 4-(5-methoxy-2-indolyl)phenyl, 4-(1-methyl-2-indolyl)-phenyl, 4-(1-methyl-5-phenyl-2-indolyl)phenyl, 4-(4,5-dichloro-2-indolyl)phenyl, 4-(2-indolyl)phenyl.

Suitable B groups are for example alkylene, arylene, carbonyloxy, oxycarbonylalkyleneoxy, such as oxycarbonylmethyleneoxy, oxycarbonylethyleneoxy, oxycarbonyl-1,4-butanediyloxy, and the like, oxycarbonyl, alkyleneoxycarbonyloxy such as methyleneoxycarbonyloxy, ethyleneoxycarbonyloxy, 1,4-butanediyloxycarbonyloxy, 1,5-pentanediyloxycarbonyloxy, and the like, oxycarbonyloxy, alkyleneoxy such as methyleneoxy, ethyleneoxy, 1,3-propanediyloxy and the like, alkyleneoxyalkyleneoxy such as methyleneoxymethyleneoxy, ethyleneoxyethyleneoxy, methyleneoxyethyleneoxy, ethyleneoxymethyleneoxy, and the like, oxyalkyleneoxy such as oxymethyleneoxy, oxyethyleneoxy, oxy-1,4-butanediyloxy and the like, thio, thioalkyleneoxy such as thiomethyleneoxy, thioethyleneoxy and the like, sulfinyldioxy, oxy(alkoxy)phosphinooxy such as oxy(methoxy)phosphinooxy, oxy(ethoxy) phosphinooxy, oxy(butoxxy)phosphinooxy and the like, alkyloxyphosphinylidene such as methoxyphosphinylidene, butoxyphosphinylidene, and the like, aryloxyphosphinylidene such as phenoxyphosphinylidene, naphoxyphosphinylidene, 3-methylphenoxyphosphinylidene, and the like, oxy(alkyl)phosphinyloxy such as oxy(methyl)phosphinyloxy, oxy(propyl)phosphinylidene, oxy(hexyl)-phosphinylidene and the like, aminocarbonyl, N-alkylaminocarbonyl such as N-methylaminocarbonyl, N-ethylaminocarbonyl, N-butylaminocarbonyl and the like, N-arylaminocarbonyl such as N-phenylaminocarbonyl, N-(3-methylphenyl)aminocarbonyl and the like, aminocarbonylalkyleneoxy such as aminocarbonylmethyleneoxy, aminocarbonyl-1,4-butanediyloxy, N-methylaminocarbonylmethyleneoxy, N-phenylaminocarbonylethyleneoxy and the like, aminocarbonylamino, N-alkylaminocarbonylamino such as N-methylaminocarbonylamino, N-ethylaminocarbonylamino and the like, di(N-alkylamino)-carbonyl such as N-methylaminocarbonyl-N'-methylamino, N-ethylaminocarbonyl-N'-methylamino, N-ethylaminocarbonyl-N'-butylamino and the like, N-arylaminocarbonylamino such as N-phenylaminocarbonylamino, N-(3-methylphenyl)aminocarbonylamino, N-arylaminocarbonyl-N'-arylamino, such as N-phenylaminocarbonyl-N'-phenylamino, alkylaminocarbonylarylamino such as N-methylaminocarbonyl-N'-phenylamino and the like, N-arylaminocarbonyl-N'-alkylamino such as N-phenylaminocarbonyl-N'-methylamino or N-methylaminocarbonyl-N'-phenylamino and the like, amino, alkyleneamino such as methyleneamino, 1,4-butanediylamino, 1,5-pentanediylamino, and the like aryleneamino such as phenyleneamino and the like, N-alkylaminoalkyleneoxy such as N-methylaminomethyleneoxy, N-ethylaminomethyleneoxy and the like, N-arylaminoalkyleneoxy such as N-phenylaminomethyleneoxy, N-phenylaminoethyleneoxy and the like, oxyalkyleneaminoalkyleneoxy such as oxymethyleneaminomethyleneoxy, oxymethyleneaminoethyleneoxy and the like, alkyleneaminocarbonylamino such as methyleneaminocarbonylamino, ethyleneaminocarbonylamino and the like, oxyalkylene(N-alkyl)aminoalkyleneoxy such as oxymethylene-(N-methyl)aminomethyleneoxy and the like, alkyleneaminoalkylene such as methyleneaminomethylene, ethyleneaminoethylene and the like, aryleneaminoarylene such as phenyleneaminophenylene and the like, aryleneaminoalkylene such as phenyleneaminomethylene and the like, alkyleneaminoarylene such as methyleneaminophenylene and the like.

Suitable C groups having the formula

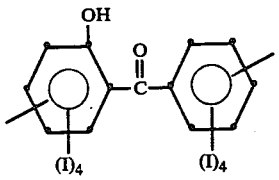

are hydroxybenzophenones, for example, 2-hydroxybenzophenone, 2,4-dihydroxybenzophenone, 2,4-dihydroxy-4'-methylbenzophenone, 5-chloro-2,2'-dihydroxybenzophenone, 2,3'-dihydroxybenzophenone, 2,5-dihydroxybenzophenone, 4-amino-2-hydroxybenzophenone, 2,2',6,6'-tetrahydroxybenzophenone, and 2,2'-dihydroxybenzophenone.

The heterocyclic compositions can be added to organic compositions which are susceptible to ultraviolet degradation. Such compositions include, for example, polymeric compositions such as polyester fiber and molding compositions, such as polyethylene terephthalate, polymethylene terephthalate and the like; polyolefins such as, for example, high, medium and low density polyethylene, polypropylene, polybutene and the like; polyamides such as N-methoxymethyl polyhexamethylene adipamide and the like; polycarbonates; polyvinyl chlorides and copolymers; cellulose esters; acrylic/butadiene/styrene plastic; polyacrylics such as methyl methacrylate; polystyrene; gelatin; vinylidene chloride copolymers such as vinylidene chloride/vinyl acetate copolymers; ethylene vinyl acetate copolymers; cellulose ethers such as methyl cellulose; polyvinyl esters such as polyvinyl acetate; polyethylene oxide; polyvinyl acetals; polyformaldehydes; and polyurethanes. Such compositions also include natural and synthetic rubbers, such as polybutadiene, and unsaturated organic compositions such as oils and the like, as well as compositions containing such organic compositions.

The polychromophoric compositions, as effective ultraviolet stabilizers or screening agents, are generally used in an amount of from 0.01 to 10%, by weight, based on the weight of the organic material to which they are added. While a detectable amount of ultraviolet screening and stabilization may be obtained with amounts less than 0.01%, this amount of stabilization or screening would be of little practical utility in a commercial application. Moreover, while amounts greater than 10%, by weight, provide effective ultraviolet stability and screening, such concentrations are undesirable because of cost and the deleterious effect which such concentrations may have on the mechanical properties of the organic composition in which the stabilizer is incorporated. Preferably, the stabilizer is used in an amount of from about 0.1 to about 3%, by weight. For example, an amount of 2%, by weight, of the stabilizer effectively stabilizes cellulose acetate butyrate plastic compositions.

The ultraviolet stabilized organic compositions of the present invention may also contain other additives, pigments, colorants, stabilizers and the like. For example, polymeric compositions, such as polyolefins, may also contain and generally do contain other additives such as white or colored pigments or colorants, antioxidants, plasticizers, flow aids, processing aids, polymeric modifiers and the like.

These novel polychromophoric ultraviolet stabilizers may be incorporated into organic compositions by melt-blending or may be added onto the surface of an organic plastic material prior to being molded into a suitable object. These materials can also be added to coatings and the like which can be applied to the surface of a molded object.

This invention will be further illustrated by the following examples although it will be understood that these examples are included merely for purposes of illustration and are not intended to limit the scope of the invention.

EXAMPLE 1

4,4′-Bis[2-[4-(2H-benzotriazol-2-yl)-2,6-xylyloxy]ethoxy]-2-hydroxybenzophenone can be prepared by the following procedure:

o-Nitroaniline (0.5 mole) was diazotized in the usual manner with concentrated hydrochloric acid (120 ml.) and sodium nitrite (0.5 mole). The clear diazonium solution was added slowly to a cold solution (0°–5° C.) of 2,6-dimethylphenol (0.5 mole) in 450 ml. of 10% sodium hydroxide. The mixture was stirred for 1 hour and Compound I filtered out (80% yield). One-tenth mole of Compound I was dissolved in 100 ml. of 2N NaOH. Zinc dust (30 g.) and sodium hydroxide (50 ml. of a 25% solution) were added slowly to the well-stirred solution. The mixture was then cooled to <30° C. and acidified with concentrated hydrochloric acid. After stirring for 2 hours, the precipitate was filtered. Compound II was recrystallized from toluene (m.p. 185°–188°, 60% yield). A mixture of the sodium salt of Compound II (0.02 mole) and 4,4′-bis(2-bromoethoxy)-2-hydroxybenzophenone (0.01 mole) in 250 ml. of ethanol was refluxed for 15 hours and product III was isolated after removal of sodium bromide by filtration.

phenol, 4-(5-chloro-2H-benzotriazol-2-yl)-2-methoxyphenol, and 4-(5-methyl-2H-benzotriazol-2-yl)-2-methoxyphenol.

Also, other polychromophoric compounds can be prepared by substituting of other hydroxybenzophenones for 4,4′-bis(2-bromoethoxy)-2-hydroxybenzophenone such as 4,4′-bis(3-bromopropoxy)-2-hydroxybenzophenone, 4,4′-bis(2-bromopropoxy)-2-hydroxybenzophenone, 4,4′-bis(2-bromoethoxy)-2,2′-dihydroxybenzophenone and 4,4′-bis(2-bromopropoxy)-2,2′-dihydroxybenzophenone.

This example hereinabove shows the B linking group as an oxyalkyleneoxy group. Other B linking groups can be provided as known in the art as for example:

1. an oxycarbonylalkyleneoxy by esterification of an acid or acid chloride with an alcohol or phenol in alkaline medium;
2. an oxycarbonyloxy by the reaction of phosgene with alcohol or phenol in alkaline medium;
3. an alkyleneoxy by the reaction of halide with alkali salt of alcohol or phenol;
4. an alkyleneoxyalkyleneoxy by the reaction of halide with alkali salt of alcohol or phenol;
5. a sulfinyldioxy by the reaction of thionyl chloride

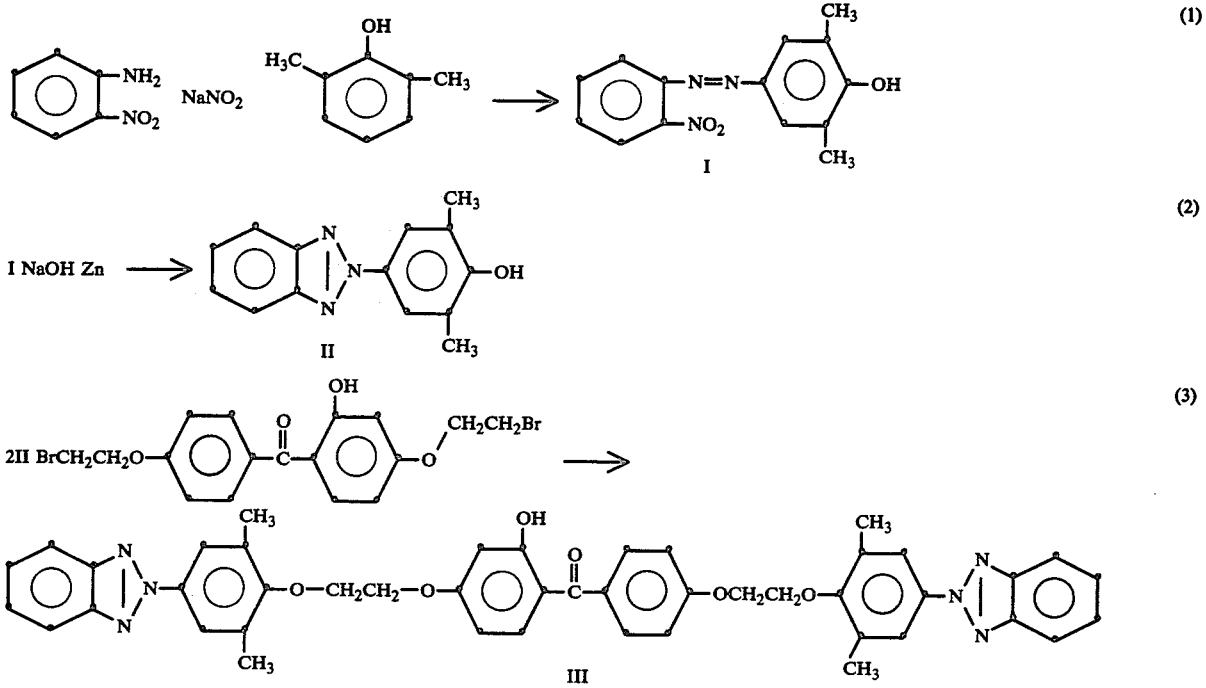

Other novel polychromophoric compounds can be prepared by substituting other benzotriazoles for 4-(2H-benzotriazol-2-yl)-2,6-dimethylphenol, such as 4-(5-chloro-2H-benzotriazol-2-yl)-2,6-dimethylphenol, 4-(5-chloro-2H-benzotriazol-2-yl)phenol, 4-(5-methyl-2H-benzotriazol-2-yl)-2,6-dimethylphenol, 4-(5-methyl-2H-benzotriazol-2-yl)-2,6-dimethylphenol, 4-(5-methyl-2H-benzotriazol-2-yl)-2-methylphenol, 4-(5-chloro-2H-benzotriazol-2-yl)-2-methylphenol, 4-(2H-benzotriazol-2-yl)-2-methylphenol, 4-(2H-benzotriazol-2-yl)-2-chlorophenol, 4-(5-chloro-2H-benzotriazol-2-yl)-2-chlorophenol, 4-(5-methyl-2H-benzotriazol-2-yl)-2-chlorophenol, 4-(2H-benzotriazol-2-yl)-2,6-dimethoxyphenol, 4-(5-chloro-2H-benzotriazol-2-yl)-2,6-dimethoxyphenol, 4-(5-methyl-2H-benzotriazol-2-yl)-2,6-dimethoxyphenol, 4-(2H-benzotriazol-2-yl)-2-methoxywith alcohol or phenol in alkaline solution;
6. a thio by the reaction of a sodium sulfide with a halide;
7. an oxy(alkoxy)phosphinooxy by the reaction of a dichlorophosphite with phenol in the presence of a base;
8. alkyl (or aryl) oxyphosphinylidene by the reaction of a halophosphate with phenol or alcohol;
9. oxy(alkyl)phosphinyloxy by the reaction of a phosphonyl chloride with phenol or alcohol;
10. an N-alkyl or N-arylaminocarbonyl by the reaction of an acid chloride with an amine;
11. an N-alkyl or N-arylaminocarbonylalkoxy by the reaction of an acid chloride with an amine;

12. an N-alkyl or N-arylaminocarbonylamino by the reaction of phosgene with an amine;
13. an N-alkyl or N-arylaminoalkylene by the reaction of an alkyl halide with an amine;
14. an N-alkyl or N-arylaminoalkyleneoxy by the reaction of an oxyalkyl halide with an amine.

EXAMPLE 2

4,4'-Bis[2-[4-(2H-benzotriazol-2-yl) phenoxy]ethoxy]-2-hydroxybenzophenone (II) can be similarly prepared by the procedure of Example I as follows:

o-Nitroaniline (138 g.) was diazotized in the usual manner with concentrated hydrochloric acid (400 ml.), water (200 ml.) and sodium nitrite (72 g.). The clear diazonium solution was added slowly to a cold solution of phenol (94 g.) in 900 ml. of 10% sodium hydroxide. The mixture was stirred for one hour and filtered, yielding 136 g. (56%) of the diazo compound (m.p. 154°–158° C.). This product was dissolved in 650 ml. of 2N sodium hydroxide solution. Zinc dust (130 g.) and sodium hydroxide (100 ml. of a 25% solution) was added slowly to the well-stirred solution. The mixture was cooled to <30° C. and acidified with concentrated hydrochloric acid. After stirring for 2 hours, the precipitate was filtered. The precipitate was taken up in a 1 liter filter of hot ethanol, solution filtered, cooled and product, p-(2H-benzotriazol2-yl)phenol, filtered out (m.p. 216°–218° C.). A well stirred mixture of p-(2H-benzotriazol-2-yl)phenol (0.02 mole) 4,4'-bis(2-bromoethoxy)-2-hydroxybenzophenone (0.01 mole), potassium carbonate (0.02 mole) and 200 ml. of methyl ethylketone were refluxed for 16 hours. The reaction mixture was washed with water. After the solvent was removed on a steam bath, 4,4'-bis[2-[4-(2H-benzotriazol-2 yl)-phenoxy]ethoxy]-2-hydroxybenzophenone was obtained.

EXAMPLE 3

Bis[4-(2H-benzotriazol-2-yl)phenyl][3-hydroxy-4,4'-carbonylbis-(p-phenyleneoxy))]bisacetate 4-(2H-Benzotriazol-2-yl)phenol (0.02 mole) (prepared as in Example 2), [3-hydroxy-4,4'-carbonyl bis(p-phenyleneoxy)]bisacetic acid (0.01 mole), boric acid (0.062 g.), sulfuric acid (0.3 ml.) and xylene (200 ml.) were stirred and refluxed overnight (the water was azeotroped out of the reaction as formed). The mixture was cooled and washed with water. The product bis[4-(2H-benzotriazol-2-yl)phenyl][3-hydroxy-4,4'-carbonyl bis(p-phenyleneoxy)]bis acetate, was obtained after removal of solvent.

EXAMPLE 4 — Preparation of 4,4'-Bis[2-[4-(2-benzoxazolyl)phenoxy] ethoxy]-2-hydroxybenzophenone (IV)

Equal molar quantities of p-hydroxybenzaldehyde and o-aminophenol in excess nitrobenzene was refluxed for 5 hours. The nitrobenzene was removed and the product extracted from the residue with xylene. 2-(4-Hydroxyphenyl)benzoxazole, m.p. 253°, was isolated in 64% yield.

The 2-(4-hydroxyphenyl) benzoxazole was reacted with 4,4'-bis(2-bromoethoxy)-2-hydroxybenzophenone as in Example 1 to produce Compound IV.

Other novel polychromophoric compounds can be prepared by substitution of other benzoxazoles for 2-(4-hydroxyphenyl)benzoxazole such as 2-(2-hydroxyphenyl)benzoxazole, 2-(3-hydroxyphenyl)benzoxazole, 2-(3-chloro-4-hydroxyphenyl)benzoxazole, 2-(3-methyl-4-hydroxyphenyl) benzoxazole, 2-(3,5-dimethyl-4-hydroxyphenyl)benzoxazole, 2-(3,5-dichloro-4-hydroxyphenyl) benzoxazole, 2-(3,5-dimethoxy-4-hydroxyphenyl)benzoxazole, 2-(2-chloro-4-hydroxy)benzoxazole, 2-(2,6-dichloro-4-hydroxyphenyl)benzoxazole and 2-(2,6-dimethyl-4-hydroxyphenyl)benzoxazole.

EXAMPLE 5 - Preparation of 4,4'-Bis[2-[4-(2-benzothiazolyl)phenoxy]ethoxy]-2-hydroxybenzophenone (V)

A hot solution of 16 g. of zinc o-aminophenylmercaptide and 125 g. of 4-hydroxybenzaldehyde in 1 liter of acetic acid was treated with hydrogen sulfide for 2 hours, filtered hot, diluted with an equal volume of water and cooled. 2-(4-Hydroxyphenyl)benzothiazole (47% yield, m.p. 227°–229°) was obtained. The 2-(4-hydroxyphenyl)benzothiazole was reacted with 4,4'-bis(2-bromoethoxy)-2-hydroxybenzophenone as in Example 1 to produce Compound V.

Other polychromophoric compounds can be prepared by substitution of other benzothiazoles for 2-(4-hydroxyphenyl)benzothiazole such as 2-(2-hydroxyphenyl)benzothiazole, 2-(3-hydroxyphenyl)benzothiazole, 2-(3-chloro-4-hydroxyphenyl)benzothiazole, 2-(3-methyl-4-hydroxyphenyl) benzothiazole, 2-(3,5-dimethyl-4-hydroxyphenyl)benzothiazole, 2-(3,5-dichloro-4-hydroxyphenyl) benzothiazole, 2-(3,5-dimethoxy-4-hydroxyphenyl)-benzothiazole, 2-(2-chloro-4-hydroxy)benzothiazole, 2-(2,6-dichloro-4-hydroxyphenyl)benzothiazole and 2-(2,6-dimethyl-4-hydroxyphenyl)-benzothiazole.

EXAMPLE 6 — Preparation of 4,4'-Bis[2-[4-(1-ethyl-2-benzimidazolyl)-phenoxy]ethoxy]-2-hydroxybenzophenone (VI).

N,N'-Bis(4-proploxybenzoyl) o-phenylenediamine (m.p. 196° C.) [prepared in 86% yield from 4-proploxybenzoyl chloride and o-phenylenediamine] was heated (200° C.) for 4 hours with concentrated hydrochloric acid. Mixture was cooled, neutralized with sodium bicarbonate and filtered. Recrystallization from ethanol gave 2-(4-hydroxyphenyl)benzimidazoles (yield 76%, m.p. 286°–288° C.).

A well-stirred mixture of 2-(4-hydroxyphenyl)benzimidazole (0.1 mole), iodoethane (0.1 mole) and sodium bicarbonate (0.12 mole) in 200 ml. of acetone was refluxed overnight. After 400 ml. of water was added, the product 2-(4-hydroxyphenyl)-1-ethylbenzimidazole (A) was filtered out. Then A was reacted with 4-bis(2-bromoethoxy)-2-hydroxybenzophenone as in Example 1 to produce Compound VI.

Other novel polychromophoric compounds can be prepared by substituting other benzimidazoles for 2-(4-hydroxyphenyl)-1-ethyl benzimidazole such as 2-(2-hydroxyphenyl)-1-ethylbenzimidazole, 2-(3-hydroxyphenyl)-1-ethylbenzimidazole, 2-(4-hydroxyphenyl)-1-phenylbenzimidazole, 2-(2-hydroxyphenyl)-1-phenylbenzimidazole, 2-(3-hydroxyphenyl)-1-phenylbenzimidazole, 2-(3,5-dichloro-4-hydroxyphenyl)-1-ethylbenzimidazole, 2-(3,5-dichloro-4-hydrophenyl)-phenylbenzimidazole, 2-(3-chloro-4-hydroxyphenyl)-1-ethylbenzimidazole, 2-(3,5-dimethoxy-4-hydroxyphenyl)-1-ethylbenzimidazole, 2-(3,5-dimethoxy-4-hydroxyphenyl)-1-phenylbenzimidazole and 2-(2-chloro-4-hydroxyphenyl)-1-ethylbenzimidazole.

EXAMPLE 7 — Preparation of 4,4'-Bis[2-[4-(1-ethyl-2-indolyl)phenoxy]-ethoxy]-2-hydroxybenzophenone (VII).

4-Hydroxyacetophenone phenylhydrazone (47 g.) was fused with 250 g. zinc chloride (10 min. at 180° C.), poured into 3 l. of 0.3 HCl, heated and stirred for 1 hour on the steam bath, cooled to 0° and filtered. The precipitant was extracted with boiling pet. ether and allowed to stand. 2-(4-Hydroxyphenyl)indole (17 g., m.p. 224°–229°) was isolated. A well-stirred mixture of 2-(4-hydroxyphenyl)indole (0.1 mole), iodoethane (0.1 mole) and sodium bicarbonate (0.12 mole) in 200 ml. of acetone was refluxed overnight. After 400 ml. of water was added, the product 2-(4-hydroxyphenyl)-1-ethylindole (A) was filtered out. Then A was reacted with 4,4'-bis(2-bromoethoxy)-2-hydroxybenzophenone as in Example 1 to produce Comound VII.

Other novel polychromophoric compounds can be prepared by substituting other indoles for 2-(4-hydroxyphenyl)-1-ethylindole such as 2-(2-hydroxyphenyl)-1-ethylindole, 2-(3-hydroxyphenyl)-1-ethylindole, 2-(4-hydroxyphenyl)-1-phenylindole, 2-(2-hydroxyphenyl)-1-phenylindole, 2-(3,5-dimethyl-4-hydroxyphenyl)-1-ethylindole, 2-(3,5-dimethyl-4-hydroxyphenyl)-1-phenylindole, 2-(3,5-dichloro-4-hydroxyphenyl)-1-ethylindole, 2-(3,5-dichloro-4-hydroxyphenyl)-1-phenylindole, 2-(3,5-dimethoxy-4-hydroxyphenyl)-1-ethylindole, 2-(3,5-dimethoxy-4-hydroxyphenyl)-1-phenylindole, 2-(2-chloro-4-hydroxyphenyl)-1-ethylindole, 2-(2-methyl-4-hydroxyphenyl)-1-ethylindole, 2-(2-hydroxy-4-methylphenyl)-1-ethylindole and 2-(2-hydroxy-4-chlorophenyl)-1-ethylindole.

EXAMPLE 8 — Preparation of a Mixed Multichromophoric Stabilizer VIII

A mixture of 2-(4-hydroxyphenyl)benzoxazole (0.01 mole), 2-(4-hydroxyphenyl)benzothiazole (0.01 mole) and 4,4'-bis(2-bromoethoxy)-2-hydroxybenzophenone (0.01 mole), potassium carbonate (0.02 mole) and 200 ml of methyl ethyl ketone were refluxed for 24 hours. After cooling, 400 ml. of water was added to the reaction mixture and the product filtered out. The product, (VIII), was used without further purification.

EXAMPLE 9

The ultraviolet stabilization provided by the heterocyclic compound of the present invention is shown for poly(tetramethylene terephthalate) in Table 1.

TABLE 1$^a$
Effectiveness of Ultraviolet Stabilizers In Poly(tetramethylene terephthalate)

| Additive (0.5%) | Flatwise Impact Strength After Mercury Lamp Exposure for Hours Indicated | | |
|---|---|---|---|
| | 0 hr. | 300 hr. | 500 hr. |
| None | 20 | 3 | 1 |
| I | 19 | 19 | 19 |
| II | 17 | 19 | 16 |
| III | 17 | 16 | 14 |
| IV | 18 | 18 | 15 |
| V | 20 | 21 | 17 |
| VI | 20 | 19 | 12 |
| VII | 17 | 17 | 16 |
| VIII | 17 | 20 | 14 |

A dry mixture of the stabilizer and granulated poly(tetramethylene terephthalate) were extruded into 1/16-inch diameter rods, pelletized and injection molded into 2½- × ½- × 1/16-inch flat bars; these flat bars were exposed to a 280–700 nm. mercury lamp source until a flatwise impact strength of less than 6 was obtained (initial values were all >17).

The test results are summarized in Table 1.

These polychromophoric compositions find particular utility as ultraviolet stabilizers in organic compositions requiring ultraviolet stability. Such compositions include polymeric compositions such as, for example, polyester fiber and molding compositions, poly-α-olefins, polyamides, acrylics, cellulose esters and the like, as well as molded or shaped articles, film and coatings formed from such materials and the like. Such compositions also include natural and synthetic rubbers, such as natural rubber, as well as organic materials such as oils, fats, and unsaturated organic materials and materials having such materials contained therein such as paints, varnishes, cosmetics and the like.

The invention has been described in detail with particular reference to preferred embodiments thereof, but it will be understood that variations and modifications can be effected within the spirit and scope of the invention.

We claim:

1. An organic composition susceptible to ultraviolet light degradation stabilized against such degradation with a stabilizing amount of at least one polychromophoric compound having the formula:

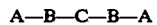

wherein A is a member of the group consisting of benzoxazoles, benzothiazoles, benzotriazoles, benzimidazoles, and indoles having the structure

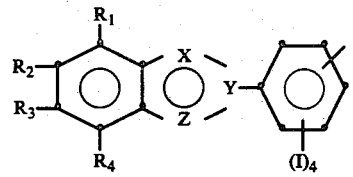

wherein

X and Y are a carbon atom or a nitrogen atom;

Z is an oxygen atom, a sulfur atom, a nitrogen atom, or a nitrogen atom containing a hydrogen atom or an unsubstituted or substituted lower alkyl group having 1 to 12 carbon atoms or an aryl group or substituted aryl group having 6 to 18 carbon atoms;

$R_1$, $R_2$, $R_3$ and $R_4$ are hydrogen, hydroxy, chloro, bromo, lower alkyl, cycloalkyl, phenyl, substituted phenyl, lower alkyl phenyl, alkoxy, amino, cyano, and carboxy;

$I$ is the same as $R_1$, $R_2$, $R_3$ and $R_4$ and is present on all positions of the benzenoid ring, except the carbon atom attached to the Y substituent and the carbon atom attached to the B group connecting the heterocyclic aromatic A group with the aromatic C group, said B connecting group is attached to the benzenoid ring in the ortho, meta or para positions from the carbon atom connected to the Y substituent, said I substituents can all be one of the substituents listed above or different listed substituents;

wherein B is a linking group connecting A and C and can be alkylene, arylene, carbonyloxy, oxycarbonylalkyleneoxy, oxycarbonyl, alkyleneoxycarbonyloxy, oxyalkylenecarbonyloxy, oxycarbonyloxy, alkyleneoxy, oxyalkylene, alkyleneoxyalkyleneoxy, thio, thioalkyleneoxy, sulfinyldioxy, oxy(alkoxy)phosphinooxy, alkyloxyphosphinylidene, aryloxyphosphinylidene, oxy(alkyl)phosphinyloxy, aminocarbonyl, N-alkylaminocarbonyl, N-arylaminocarbonyl, aminocarbonylalkyleneoxy, N-alkylaminocarbonylalkyleneoxy, N-arylaminocarbonylalkyleneoxy, aminocarbonylamino, N-alkylaminocarbonylamino, N,N-dialkylaminocarbonyl, N-arylaminocarbonyl, N-alkylaminocarbonyl, N,N-diarylaminocarbonyl, amino, N-alkylamino, N-arylamino, N-alkylaminoalkyleneoxy, N-arylaminoalkyleneoxy, oxyalkyleneoxy, oxyaryleneoxy, alkyleneaminoarylene, aryleneaminoarylene, aryleneaminoalkylene and alkyleneaminoarylene; and wherein C is a hydroxybenzophenone group having the formula

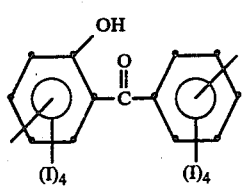

I is the same substituent as listed above and is present in all positions of the benzenoid rings except the carbon atom attached to the B group connecting the A and C moieties, and the B connecting group is attached to the benzenoid ring in the ortho, meta or para position from the keto group of the benzophenone, and said I substituents can all be one of the substituents listed above or different listed substituents.

2. An organic composition according to claim 1 wherein said polychromophoric compound has the formula:

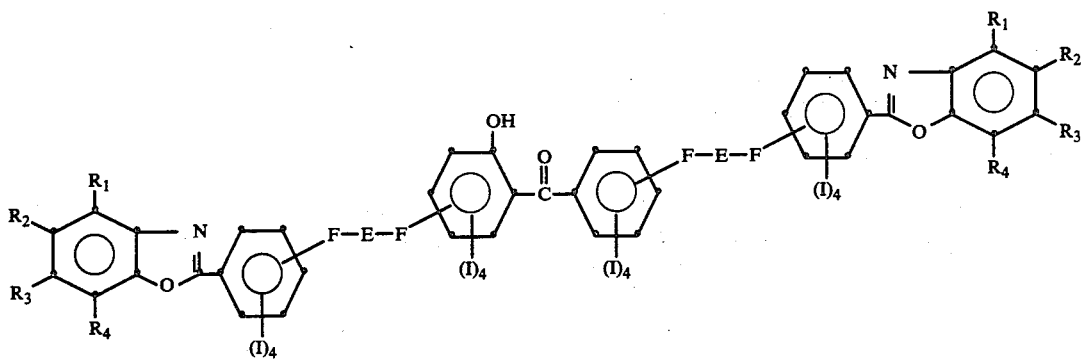

wherein E is a member selected from the group consisting of an alkylene group or cycloalkylene group containing 1 to 8 carbon atoms, carbonyl alkylene, alkylene carbonyl and F is oxygen, nitrogen or sulfur;

$R_1$, $R_2$, $R_3$ and $R_4$ are hydrogen, hydroxy, chloro, bromo, lower alkyl, cycloalkyl, aryl, substituted aryl, lower alkylaryl, alkoxy, amino, cyano, and carboxy;

I is the same as $R_1$, $R_2$, $R_3$ and $R_4$ and is present on all positions of the benzenoid ring, except the carbon atom attached to the FEF substituent, said I substituents can all be one of the substituents listed above or different listed substituents.

3. An organic composition according to claim 2 wherein said polychromophoric compound has the formula:

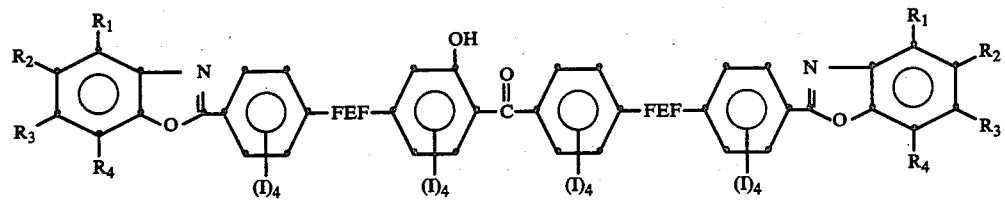

wherein E is a member selected from the group consisting of an alkylene group or cycloalkylene group containing 1 to 8 carbon atoms, carbonyl alkylene, alkylene carbonyl and F is oxygen, nitrogen, or sulfur;

$R_1$, $R_2$, $R_3$ and $R_4$ are hydrogen, hydroxy, chloro, bromo, lower alkyl, cycloalkyl, aryl, substituted aryl, lower alkylaryl, alkoxy, amino, substituted amino, cyano, and carboxy;

I is the same as $R_1$, $R_2$, $R_3$ and $R_4$ and is present on all positions of the benzoid ring, except the carbon atom attached to the FEF substituent, said I substituents can all be one of the substituents listed above or different listed substituents.

4. An organic composition according to claim 3 wherein said polychromophoric compound has the formula:

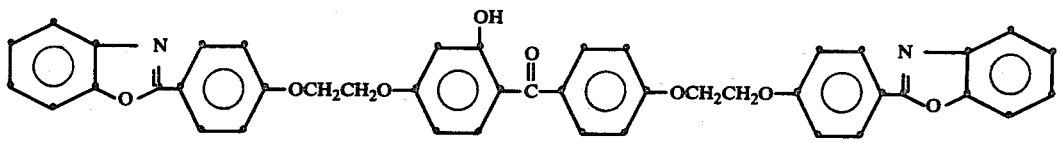

5. An organic composition according to claim 3 wherein said polychromophoric compound has the formula:

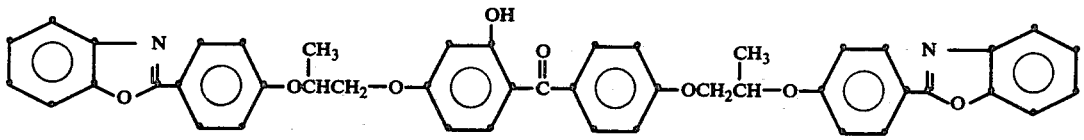

6. An organic composition according to claim 3 wherein said polychromophoric compound has the formula:

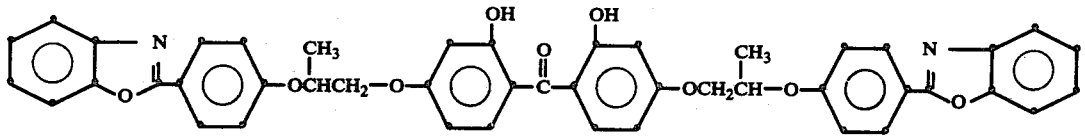

7. An organic composition according to claim 3 wherein said polychromophoric compound has the formula:

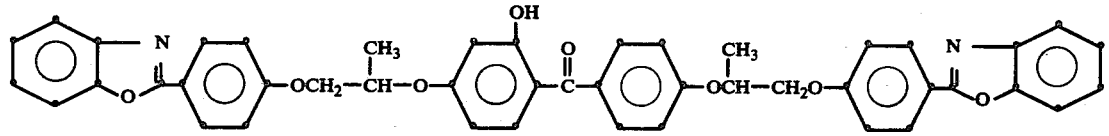

8. An organic composition according to claim 3 wherein said polychromophoric compound has the formula:

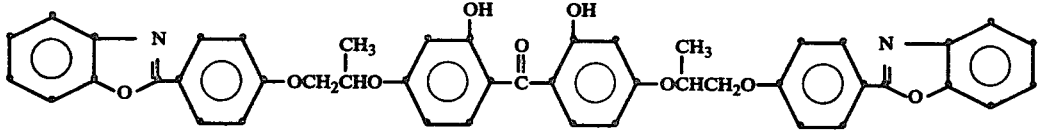

9. An organic composition according to claim 3 wherein said polychromophoric compound has the formula:

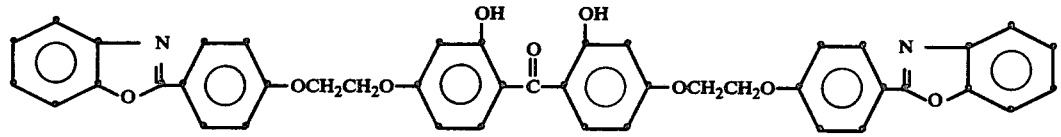

10. An organic composition according to claim 3 wherein sia polychromophoric compound has the formula:

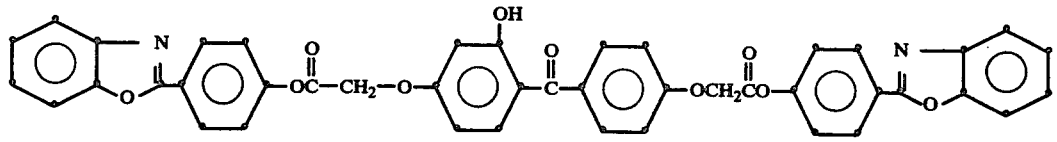

11. An organic composition according to claim 3 wherein said polychromophoric compound has the formula:

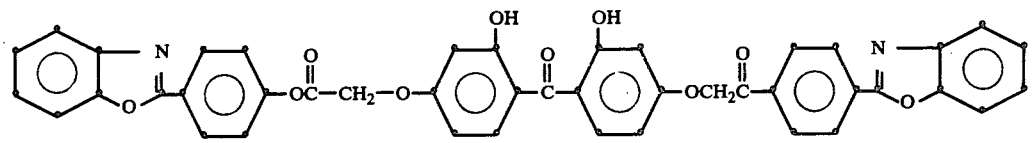

12. An organic composition according to claim 3 wherein said polychromophoric compound has the formula:

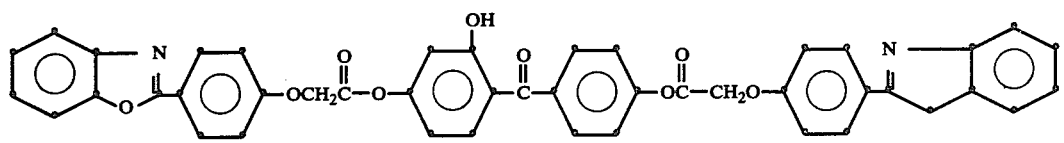

13. An organic composition according to claim 3 wherein said polychromophoric compound has the formula:

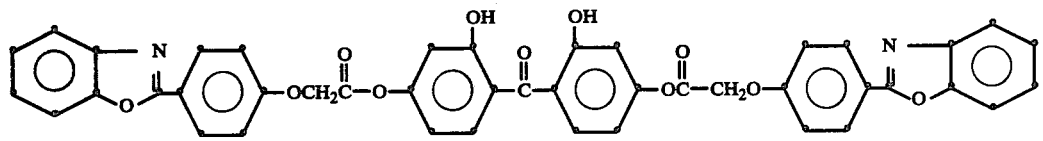

14. An organic composition according to claim 3 wherein said polychromophoric compound has the formula:

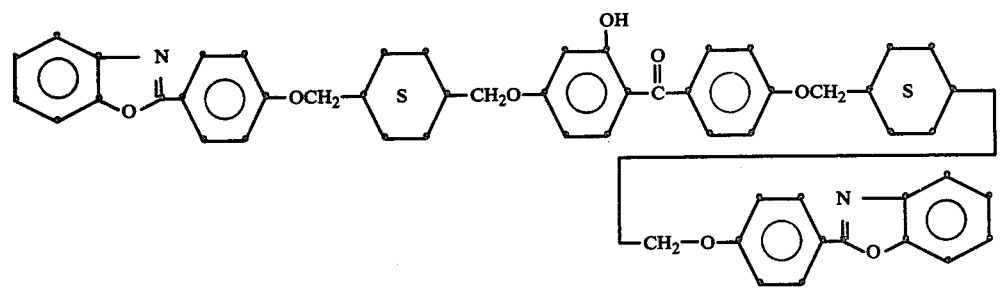

15. An organic composition according to claim 3 wherein said polychromophoric compound has the formula:

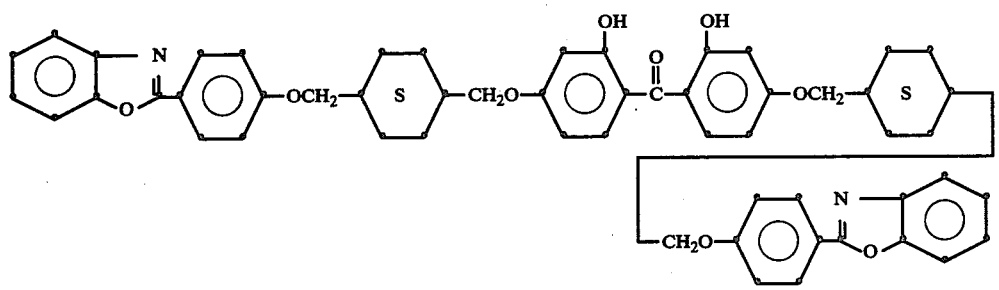

16. An organic composition according to claim 3 wherein said polychromophoric compound has the formula:

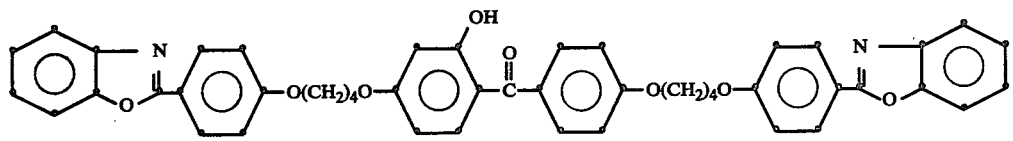

17. An organic composition according to claim 3 wherein said polychromophoric compound has the formula:

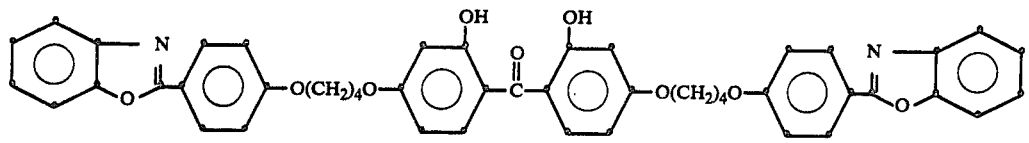

18. An organic composition according to claim 3 wherein said polychromophoric compound has the formula:

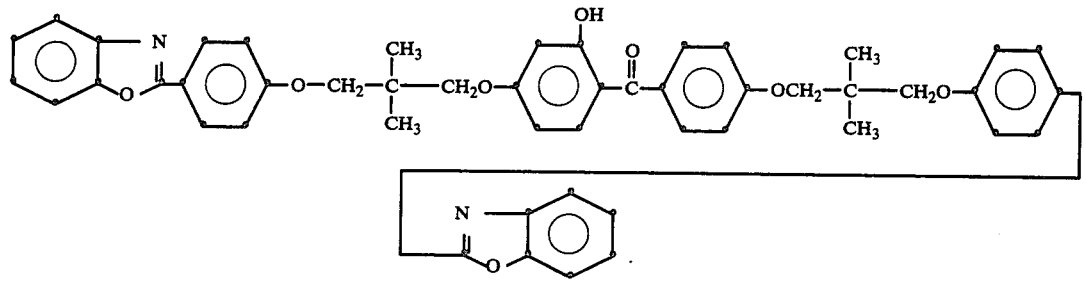

19. An organic composition according to claim 3 wherein said polychromophoric compound has the formula:

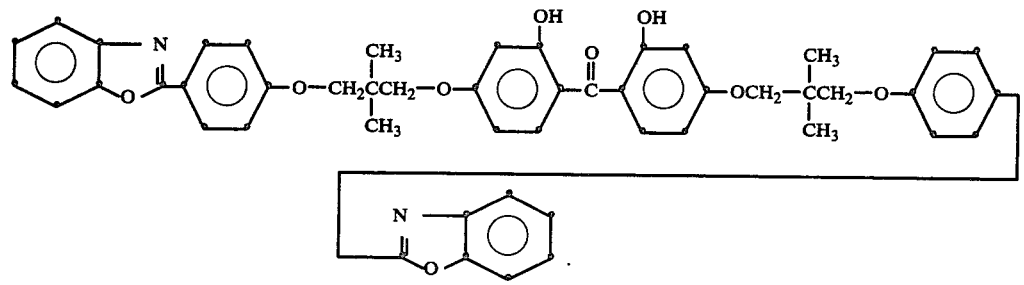

20. An organic composition according to claim 1 wherein Z of sai polychromophoric compound is a nitrogen atom.

21. A composition of matter according to claim 20 wherein said polychromophoric compound has the formula:

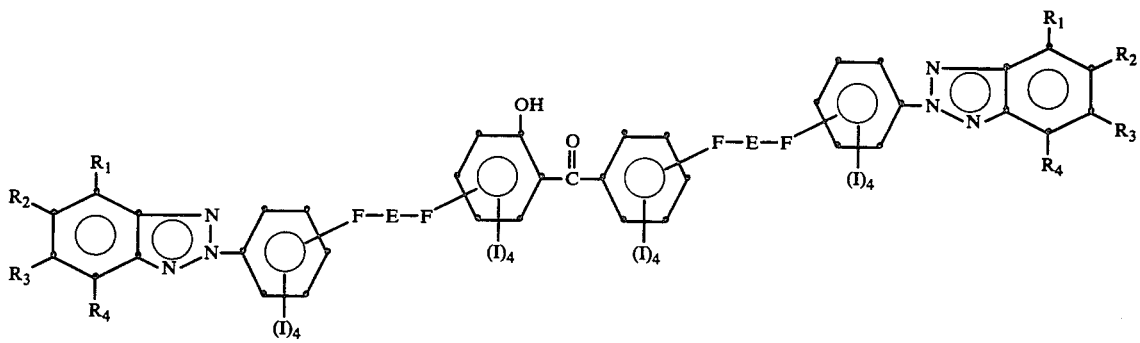

wherein E is a member selected from the group consisting of an alkylene group or cycloalkylene group containing 1 to 8 carbon atoms, carbonyl alkylene, alkylene carbonyl and F is oxygen, nitrogen or sulfur;

$R_1$, $R_2$, $R_3$ and $R_4$ are hydrogen, hydroxy, chloro, bromo, lower alkyl, cycloalkyl, phenyl, lower alkyl phenyl, alkoxy, amino, cyano, carboxy;

I is the same as $R_1$, $R_2$, $R_3$ and $R_4$ and is present on all positions of the benzenoid ring, except the carbon atom attached to the FEF substituent, said I substituents can all be one of the substituents listed above or different listed substituents.

22. An organic composition according to claim 21 wherein said polychromophoric compound has the formula:

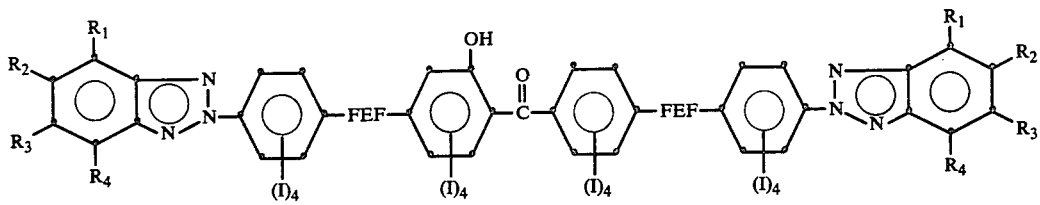

wherein E is a member selected from the group consisting of an alkylene group or cycloalkylene group containing 1 to 8 carbon atoms, carbonyl alkylene, alkylene carbonyl and F is oxygen, nitrogen or sulfur;

$R_1$, $R_2$, $R_3$ and $R_4$ are hydrogen, hydroxy, chloro, bromo, lower alkyl, cycloalkyl, phenyl, lower alkyl phenyl, alkoxy, amino, cyano, carboxy;

I is the same as $R_1$, $R_2$, $R_3$ and $R_4$ and is present on all positions of the benzenoid ring, except the carbon atom attached to the FEF substituent, said I substituents can all be one of the substituents listed above or different listed substituents.

23. An organic composition according to claim 22 wherein said polychromophoric compound has the formula:

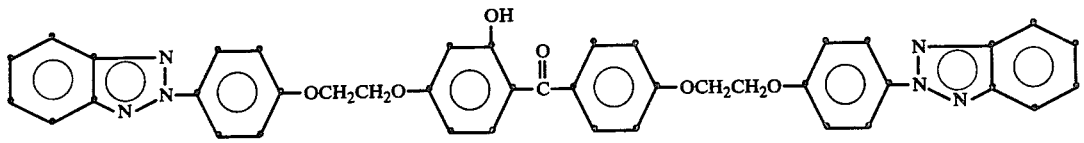

24. An organic composition according to claim 22 wherein said polychromophoric compound has the formula:

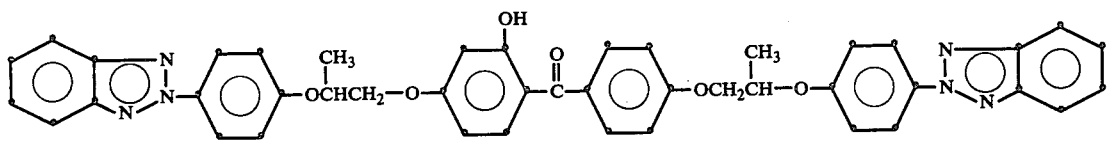

25. An organic composition according to claim 22 wherein said polychromophoric compound has the formula:

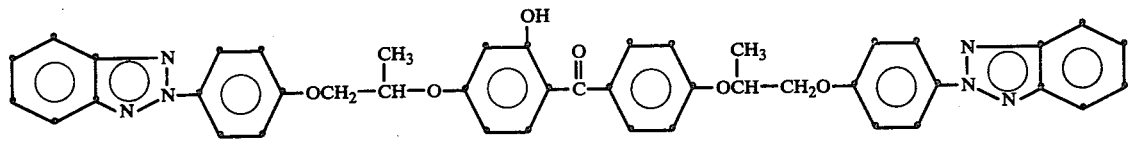

26. An organic composition according to claim 22 wherein said polychromophoric compound has the formula:

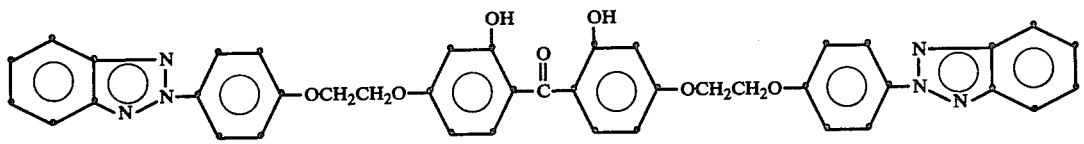

27. An organic composition according to claim 22 wherein said polychromophoric compound has the formula:

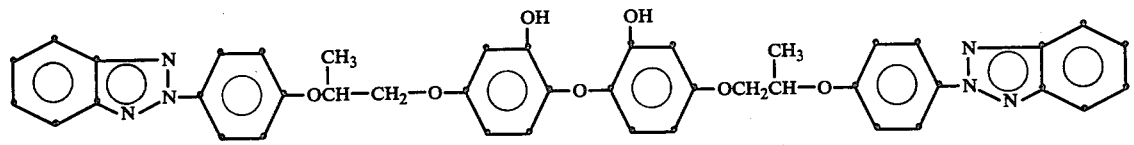

28. An organic composition according to claim 22 wherein said polychromophoric compound has the formula:

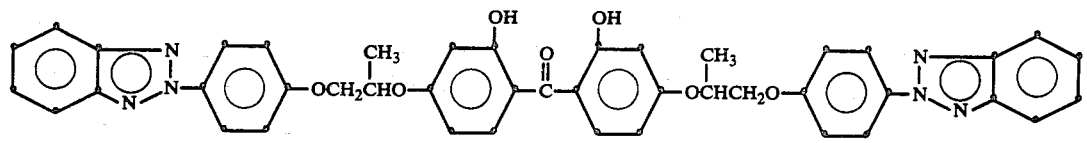

29. An organic composition according to claim 22 wherein said polychromophoric compound has the formula:

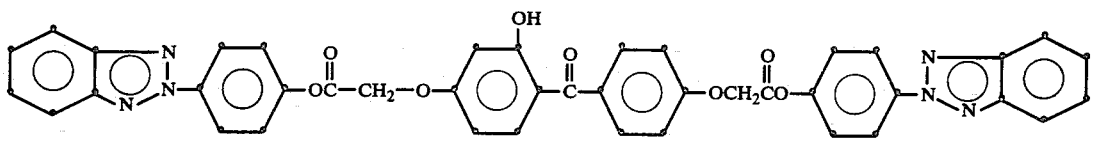

30. An organic composition according to claim 22 wherein said polychromophoric compound has the formula:

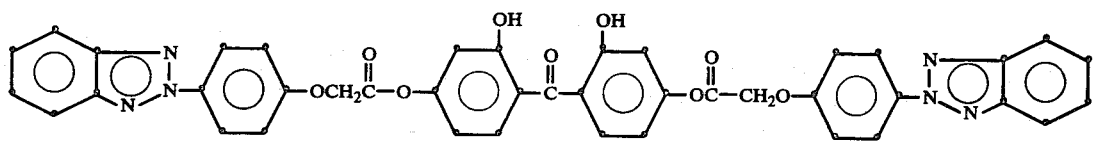

31. An organic composition according to claim 22 wherein said polychromophoric compound has the formula:

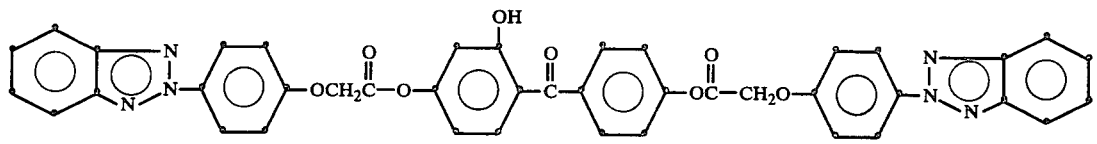

32. An organic composition according to claim 22 wherein said polychromophoric compound has the formula:

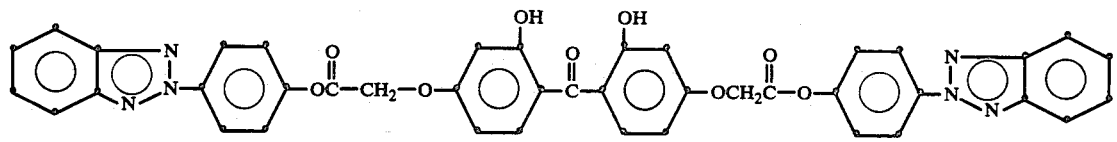

33. An organic composition according to claim 22 wherein said polychromophoric compound has the formula:

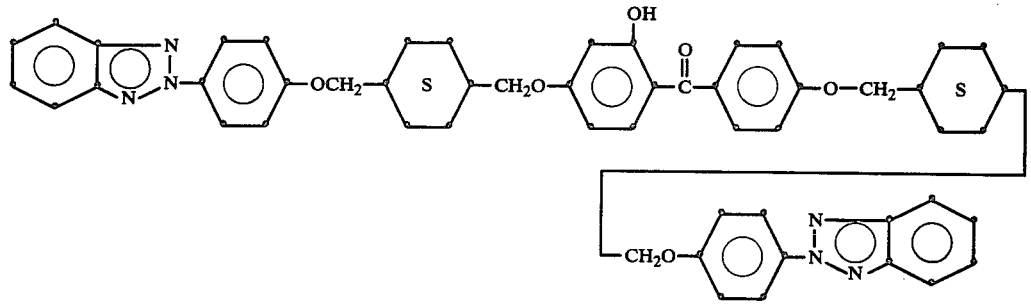

34. An organic composition according to claim 22 wherein said polychromophoric compound has the formula:

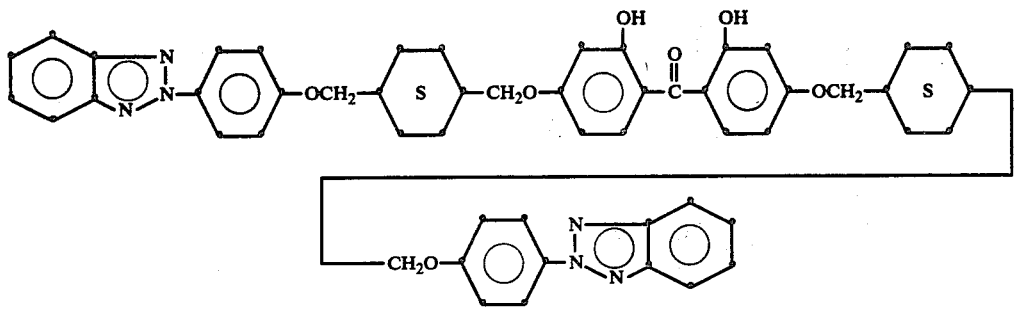

35. An organic composition according to claim 22 wherein said polychromophoric compound has the formula:

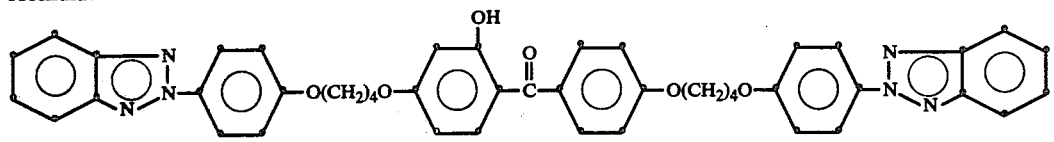

36. An organic composition according to claim 22 wherein said polychromophoric compound has the formula:

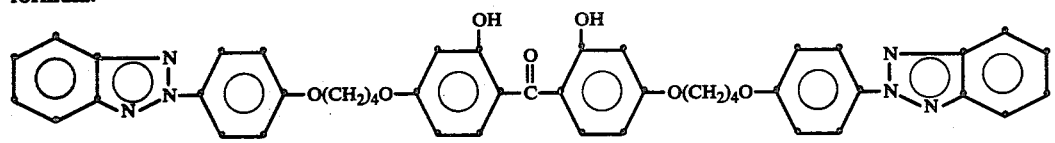

37. An organic composition according to claim 22 wherein said polychromophoric compound has the formula:

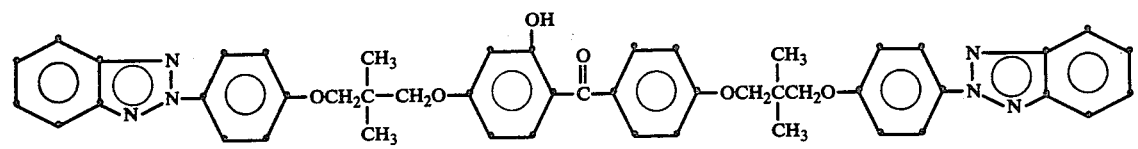

38. An organic composition according to claim 22 wherein said polychromophoric compound has the formula:

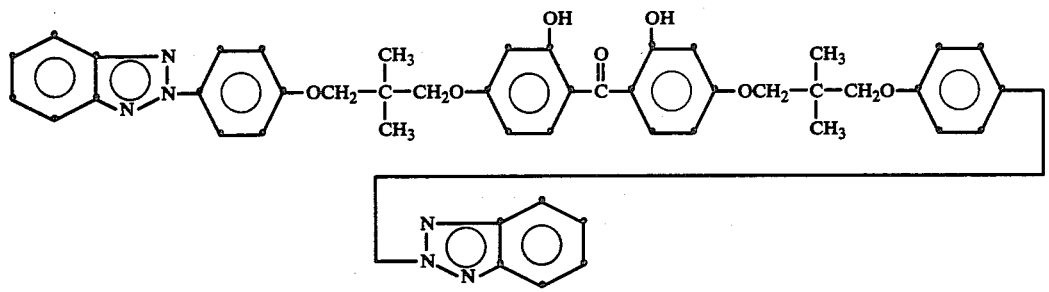

39. An organic composition according to claim 22 wherein said polychromophoric compound has the formula:

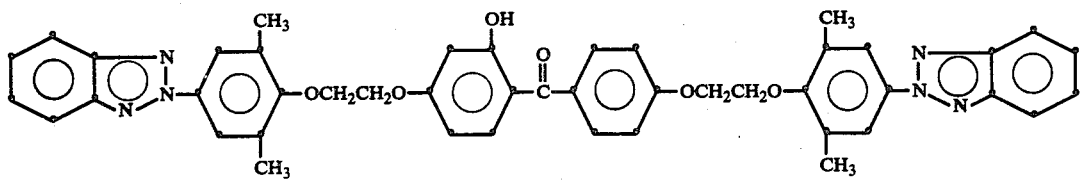

40. An organic composition according to claim 22 wherein said polychromophoric compound has the formula:

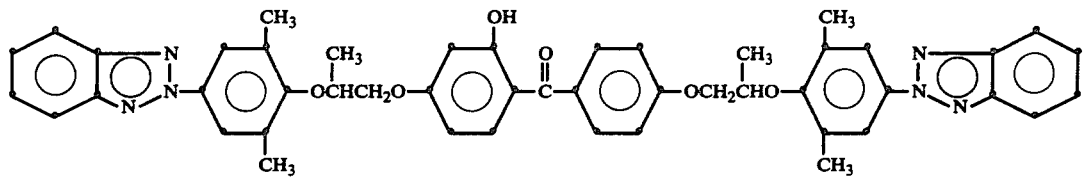

41. An organic composition according to claim 22 wherein said polychromophoric compound has the formula:

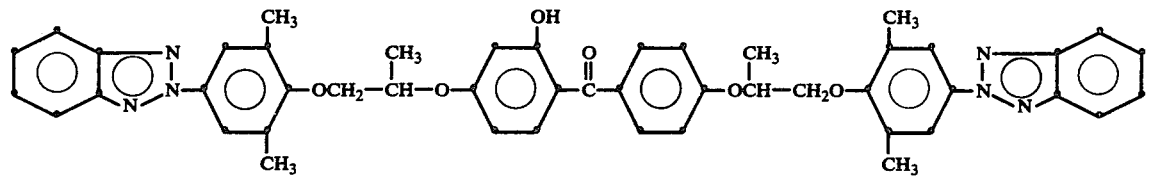

44. An organic composition according to claim 22 wherein said polychromophoric compound has the formula:

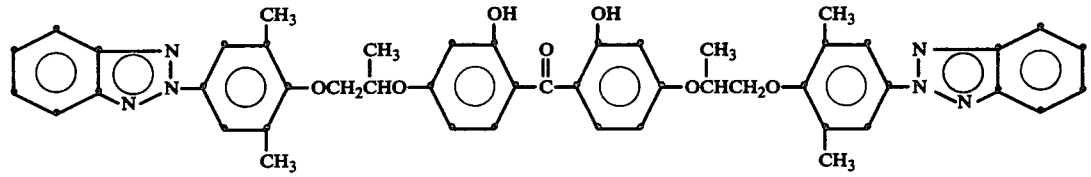

42. An organic composition according to claim 22 wherein said polychromophoric compound has the formula:

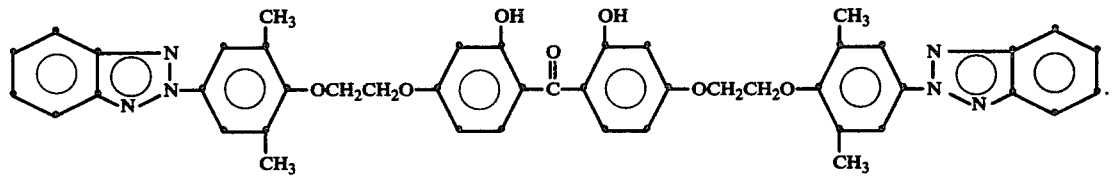

45. An organic composition according to claim 22 wherein said polychromophoric compound has the formula:

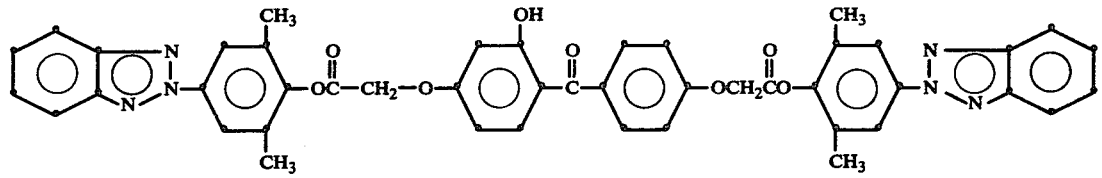

43. An organic composition according to claim 22 wherein said polychromophoric compound has the formula:

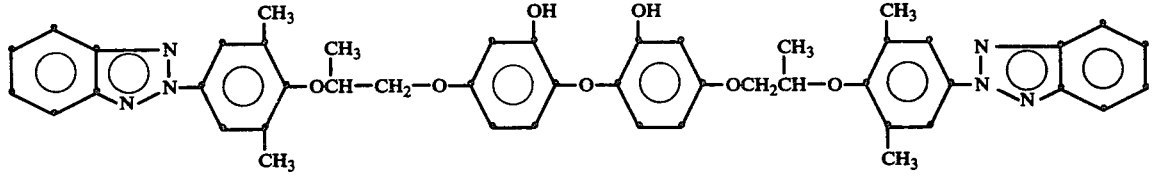

46. An organic composition according to claim 22 wherein said polychromophoric compound has the formula:

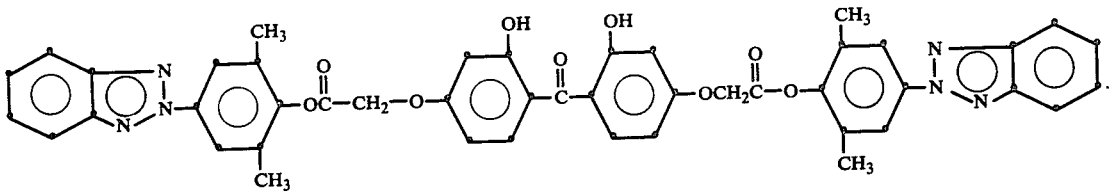

47. An organic composition according to claim 22 wherein said polychromophoric compound has the formula:

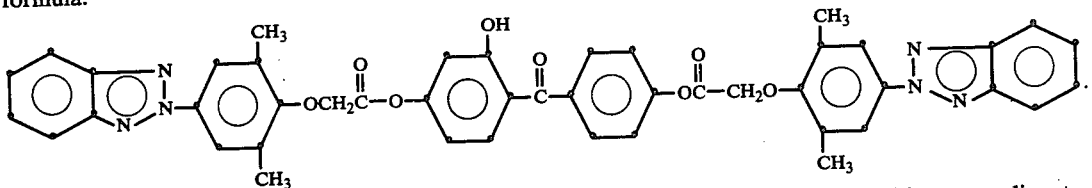

48. An organic composition according to claim 22 wherein said polychromophoric compound has the formula:

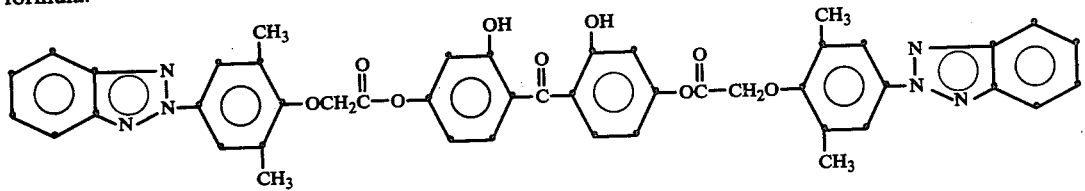

49. An organic composition according to claim 22 wherein said polychromophoric compound has the formula:

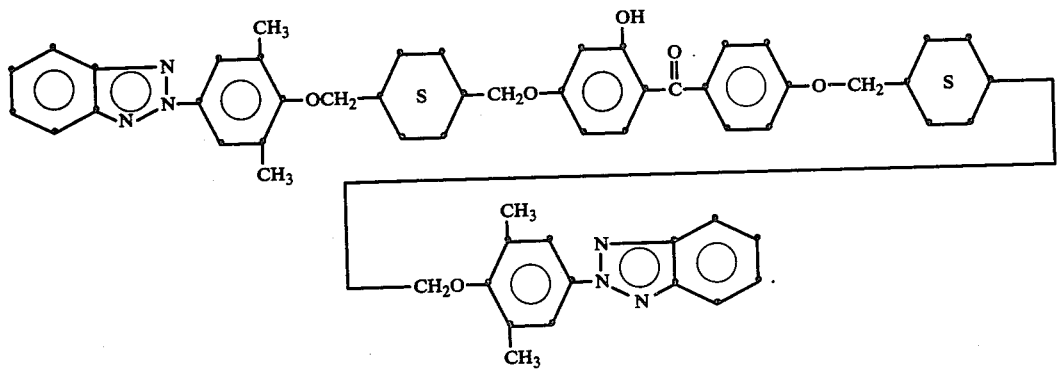

50. An organic composition according to claim 22 wherein said polychromophoric compound has the formula:

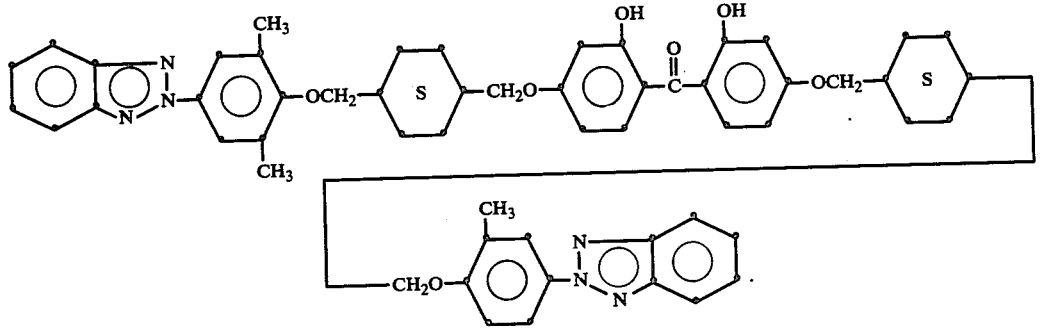

51. An organic composition according to claim 22 wherein said polychromophoric compound has the formula:

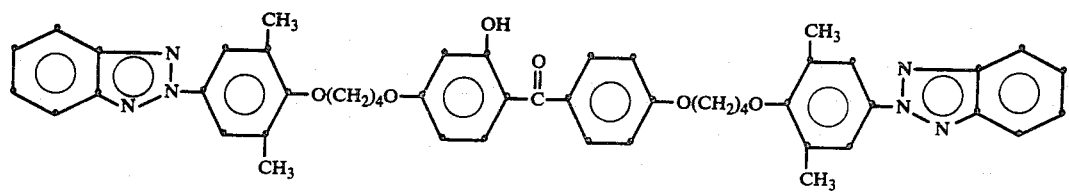

52. An organic composition according to claim 22 wherein said polychromophoric compound has the formula:

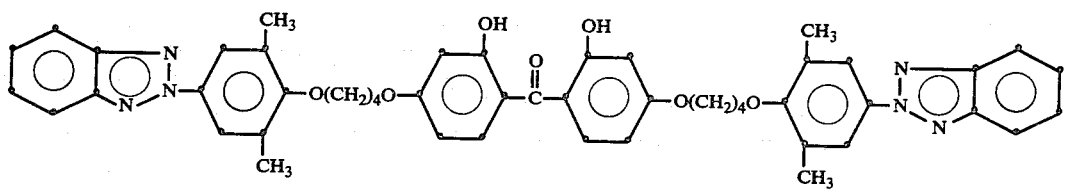

53. An organic composition according to claim 22 wherein said polychromophoric compound has the formula:

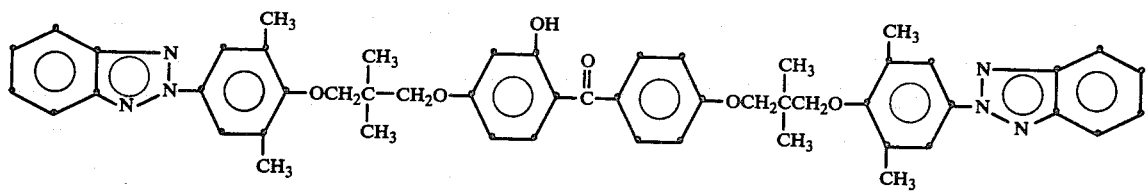

54. An organic composition according to claim 22 wherein said polychromophoric compound has the formula:

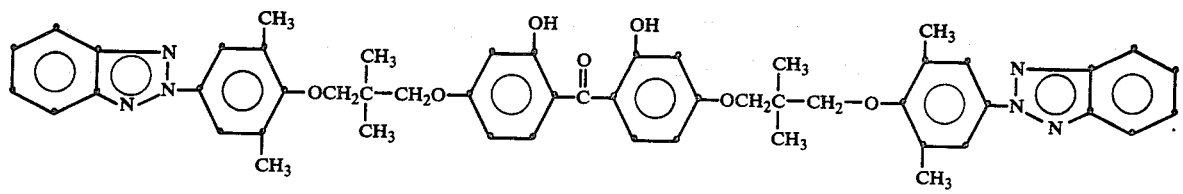

55. An organic composition according to claim 24 wherein said polychromophoric compound has the formula:

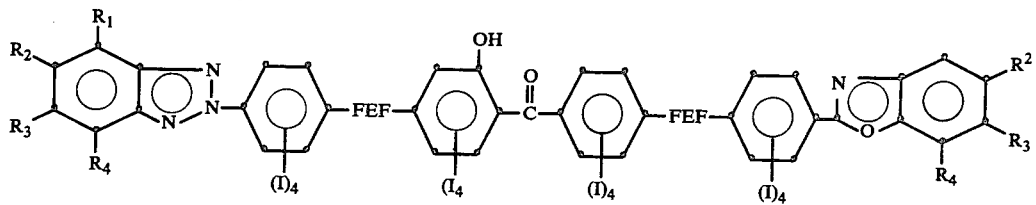

wherein E is a member selected from the group consisting of an alkyl group containing 1 to 8 carbon atoms, carbonyl alkylene, alkylene carbonyl and F is oxygen, nitrogen or sulfur;

$R_1$, $R_2$, $R_3$ and $R_4$ are hydrogen, hydroxy, chloro, bromo, lower alkyl, cycloalkyl, phenyl, lower alkyl phenyl, alkoxy, amino, cyano, carboxy;

I is the same as $R_1$, $R_2$, $R_3$ and $R_4$ and is present on all positions of the benzenoid ring, except the carbon atom attached to the FEF substituent, said I substituents can also be one of the substituents listed above or different listed substituents.

56. An organic composition according to claim 55 wherein said polychromophoric compound has the formula:

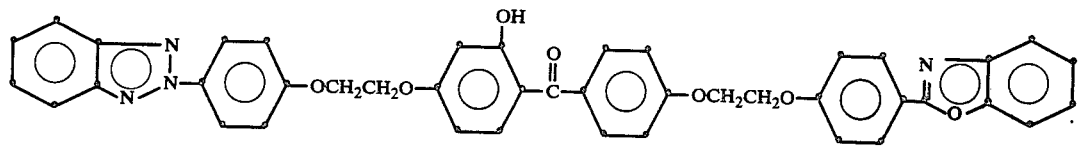

57. An organic composition according to claim 55 wherein said polychromophoric compound has the formula:

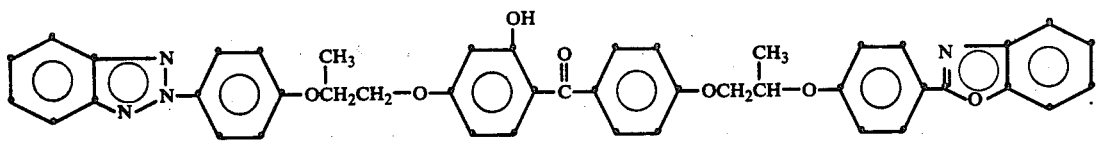

58. An organic composition according to claim 55 wherein said polychromophoric compound has the formula:

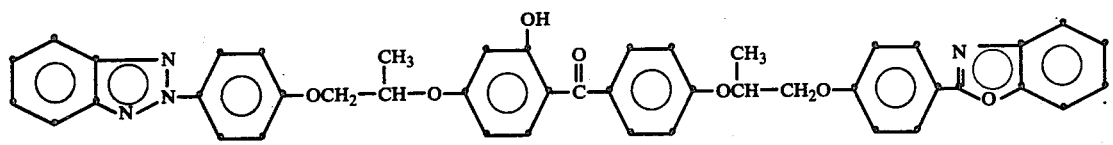

59. An organic composition according to claim 55 wherein said polychromophoric compound has the formula:

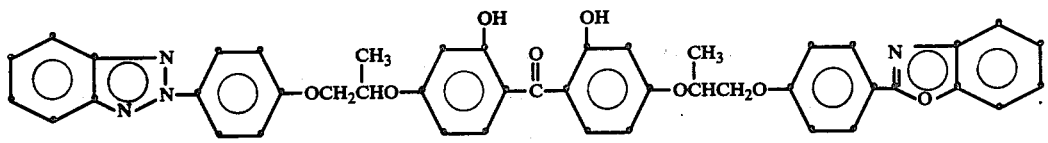

60. An organic composition according to claim 55 wherein said polychromophoric compound has the formula:

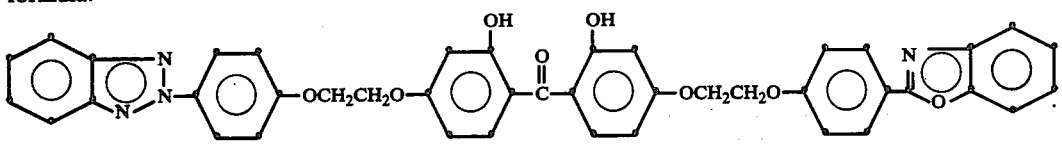

61. An organic composition according to claim 55 wherein said polychromophoric compound has the formula:

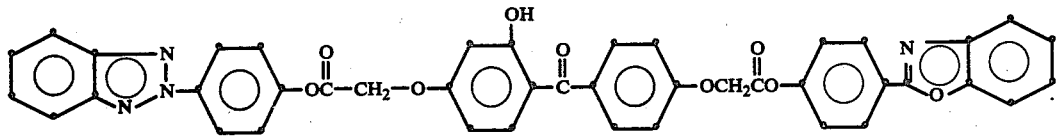

62. An organic composition according to claim 55 wherein said polychromophoric compound has the formula:

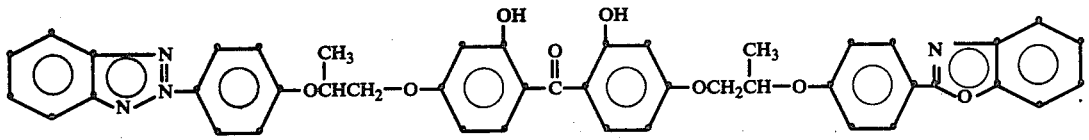

63. An organic composition according to claim 55 wherein said polychromophoric compound has the formula:

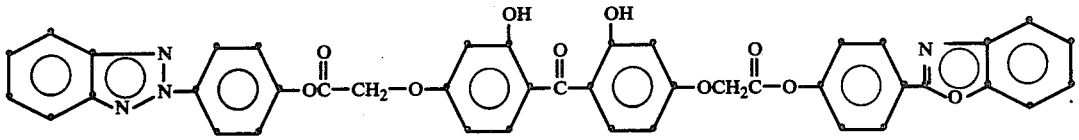

64. An organic composition according to claim 55 wherein said polychromophoric compound has the formula:

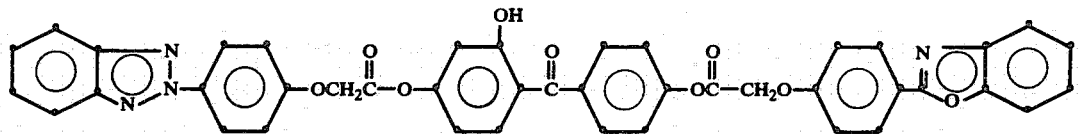

65. An organic composition according to claim 55 wherein said polychromophoric compound has the formula:

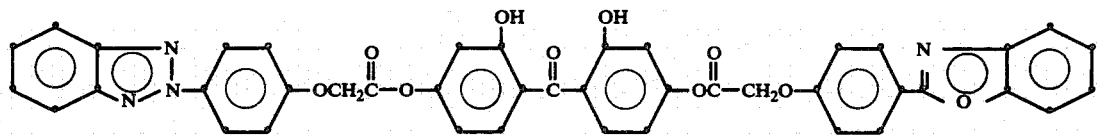

66. An organic composition according to claim 55 wherein said polychromophoric compound has the formula:

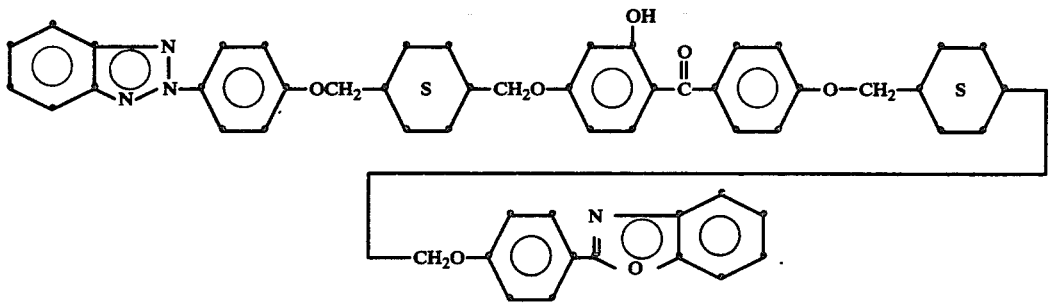

67. An organic composition according to claim 55 wherein said polychromophoric compound has the formula:

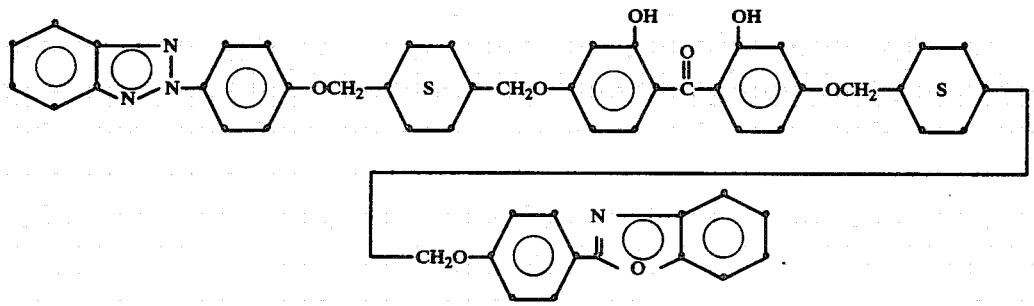

68. An organic composition according to claim 55 wherein said polychromophoric compound has the formula:

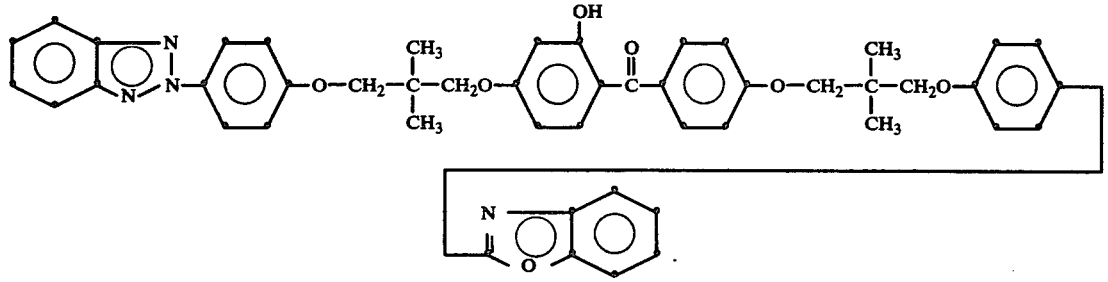

69. An organic composition according to claim 55 wherein said polychromophoric compound has the formula:

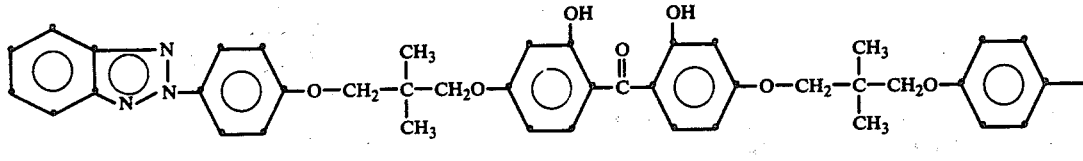

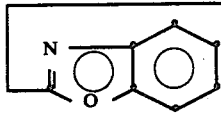

70. An organic composition according to claim 55 wherein said polychromophoric compound has the formula:

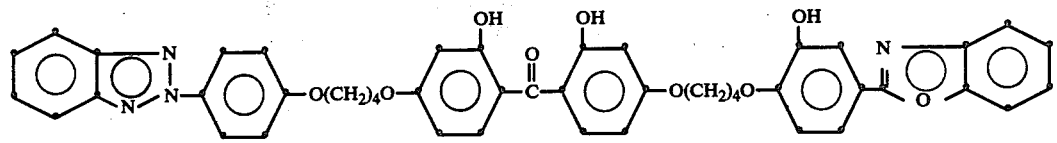

71. An organic composition according to claim 55 wherein said polychromophoric compound has the formula:

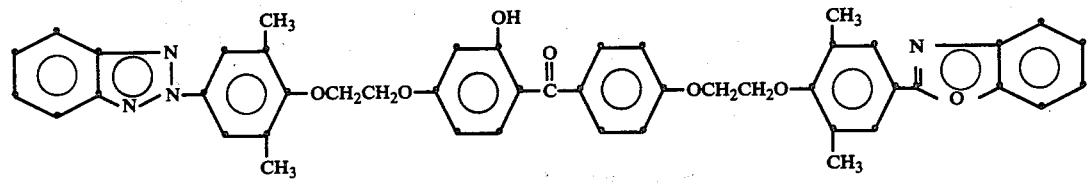

72. An organic composition according to claim 55 wherein said polychromophoric compound has the formula:

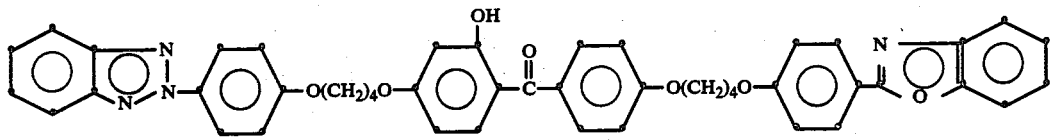

73. An organic composition according to claim 55 wherein said polychromophoric compound has the formula:

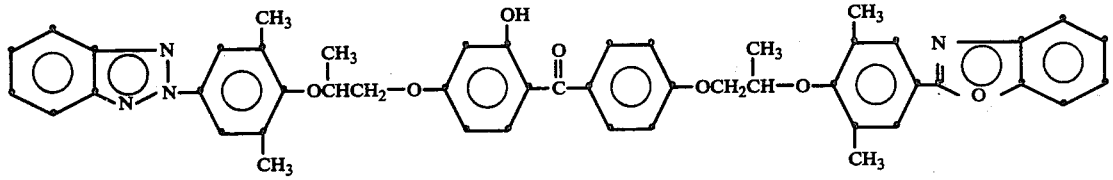

74. An organic composition according to claim 55 wherein said polychromophoric compound has the formula:

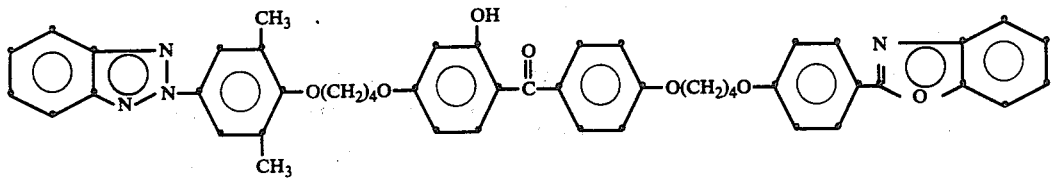

75. An organic composition according to claim 55 wherein said polychromophoric compound has the formula:

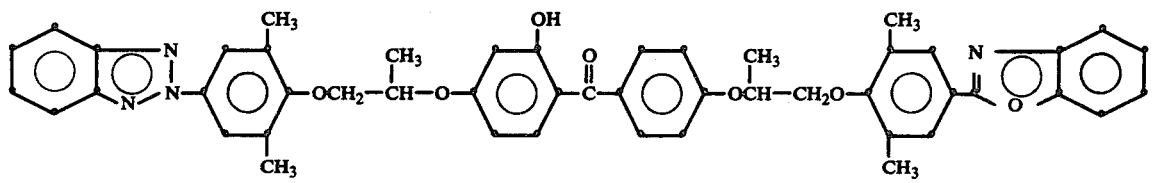

76. An organic composition according to claim 55 wherein said polychromophoric compound has the formula:

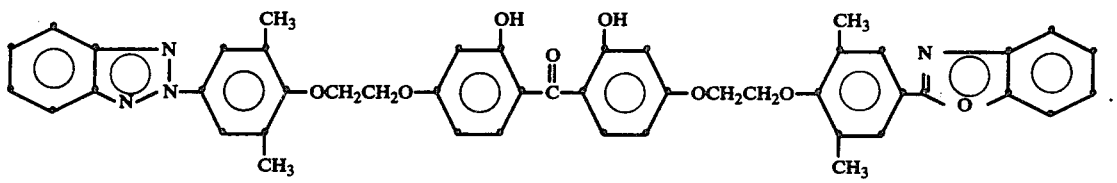

77. An organic composition according to claim 55 wherein said polychromophoric compound has the formula:

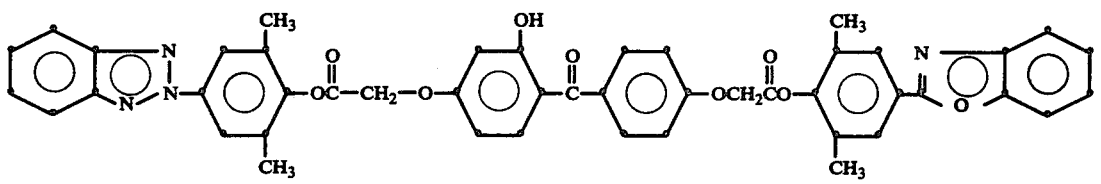

78. An organic composition according to claim 55 wherein said polychromophoric compound has the formula:

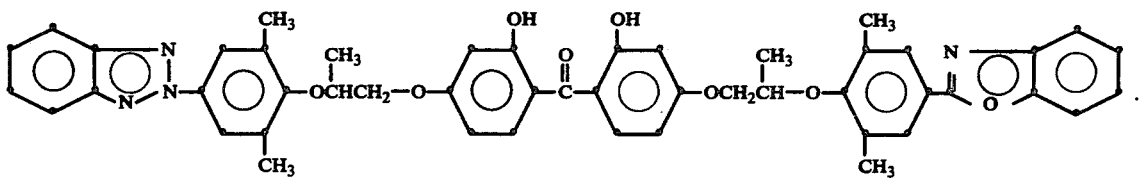

79. An organic composition according to claim 55 wherein said polychromophoric compound has the formula:

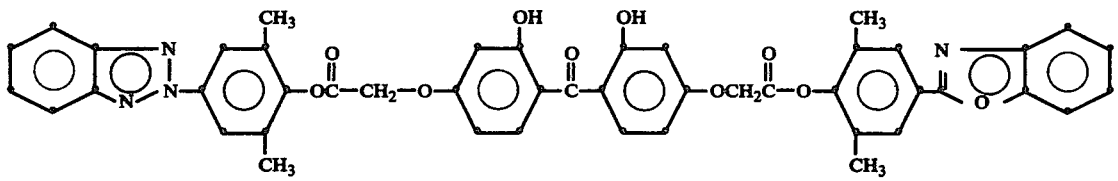

80. An organic composition according to claim 55 wherein said polychromophoric compound has the formula:

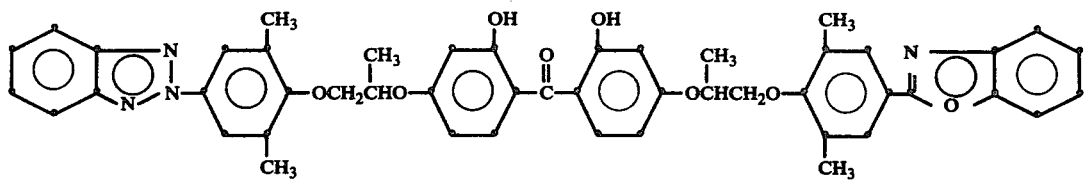

81. An organic composition according to claim 55 wherein said polychromophoric compound has the formula:

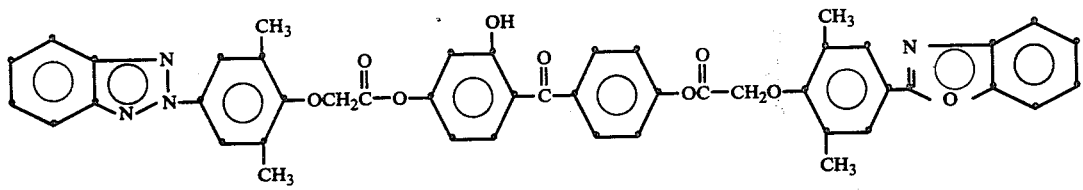

82. An organic composition according to claim 55 wherein said polychromophoric compound has the formula:

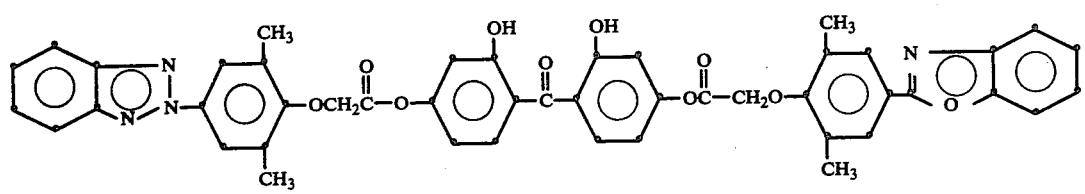

84. An organic composition according to claim 55 wherein said polychromophoric compound has the formula:

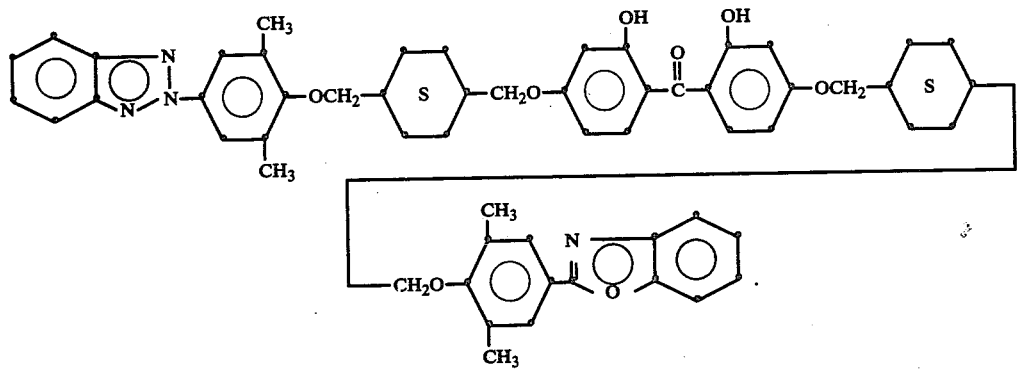

83. An organic composition according to claim 55 wherein said polychromophoric compound has the formula:

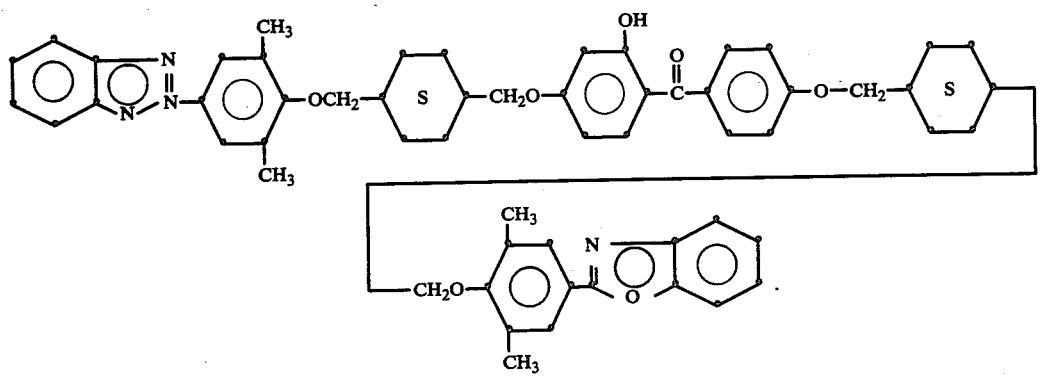

85. An organic composition according to claim 55 wherein said polychromophoric compound has the formula:

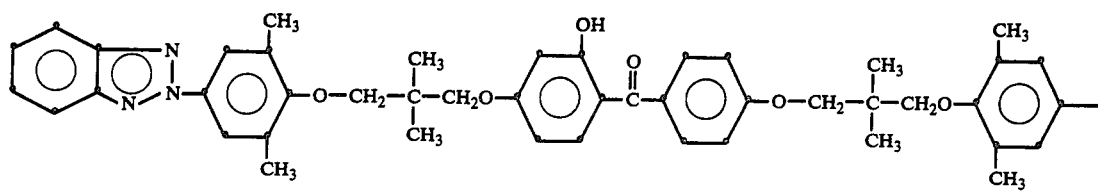
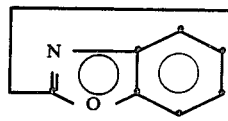
86. An organic composition according to claim 55 wherein said polychromophoric compound has the formula:
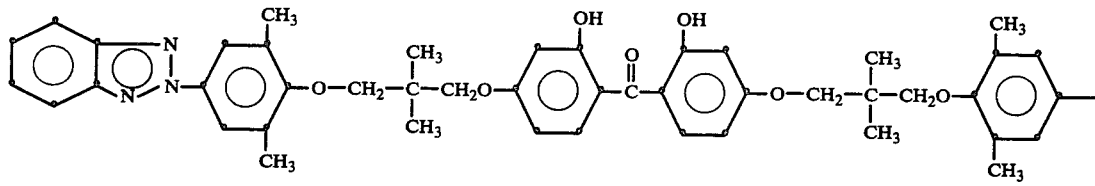
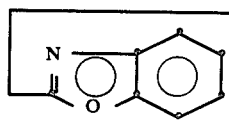
* * * * *